United States Patent
Ament et al.

(10) Patent No.: US 11,439,073 B2
(45) Date of Patent: Sep. 13, 2022

(54) **INTERSPECIFIC HYBRID PLANT RESULTING FROM A CROSS BETWEEN AN *ALLIUM AMPELOPRASUM* PLANT WITH AN *ALLIUM SATIVUM* PLANT**

(71) Applicant: Bejo Zaden B.V., Warmenhuizen (NL)

(72) Inventors: Kai Ament, Heiloo (NL); Henricus Chretien Marie Louise Bongers, Baarlo (NL); Marcel Adriaanse, Haarlem (NL); Albertus Johannes Maria Schrijver, Warmenhuizen (NL)

(73) Assignee: Bejo Zaden B.V., Warmenhuizen (NL)

( * ) Notice: Subject to any disclaimer, the term of this patent is extended or adjusted under 35 U.S.C. 154(b) by 0 days.

(21) Appl. No.: 16/476,691

(22) PCT Filed: Jan. 17, 2018

(86) PCT No.: PCT/EP2018/051085
§ 371 (c)(1),
(2) Date: Jul. 9, 2019

(87) PCT Pub. No.: WO2018/134236
PCT Pub. Date: Jul. 26, 2018

(65) Prior Publication Data
US 2020/0260676 A1    Aug. 20, 2020

(30) Foreign Application Priority Data

Jan. 19, 2017    (EP) .................................... 17152251

(51) Int. Cl.
| | | |
|---|---|---|
| *A01H 5/06* | (2018.01) | |
| *A01H 6/04* | (2018.01) | |
| *C12Q 1/68* | (2018.01) | |
| *C12Q 1/6895* | (2018.01) | |
| *A01H 5/12* | (2018.01) | |
| *A01H 5/04* | (2018.01) | |

(52) U.S. Cl.
CPC ............ *A01H 6/04* (2018.05); *A01H 5/04* (2013.01); *A01H 5/06* (2013.01); *A01H 5/12* (2013.01); *C12Q 1/6895* (2013.01); *C12Q 2600/13* (2013.01)

(58) Field of Classification Search
None
See application file for complete search history.

(56) References Cited

U.S. PATENT DOCUMENTS

| | | |
|---|---|---|
| 2011/0167509 A1 | 7/2011 | Van Cappellen et al. |
| 2015/0101074 A1 | 4/2015 | Kamenetsky Goldstein et al. |

FOREIGN PATENT DOCUMENTS

| | | | |
|---|---|---|---|
| WO | 2010007059 A1 | 1/2010 | |
| WO | WO-2010007059 A1 * | 1/2010 | ............... A01H 5/12 |
| WO | 2013128454 A1 | 9/2013 | |

OTHER PUBLICATIONS

Yanagino et al. Production and characterization of an interspecific hybrid between leek and garlic. (2003) Theor. Appl. Genet.; vol. 107; pp. 1-5 (Year: 2003).*
Merriam-Webster; definition of "as" (2021) downloaded from: https://www.merriam-webster.com/dictionary/as on Feb. 24, 2021; pp. 1-11 (Year: 2021).*
Alix et al. Polyploidy and interspecific hybridization: partners for adaptation, speciation and evolution in plants. (2017) Annals of Botany; vol. 120; pp. 183-194 (Year: 2017).*
Ohsumi et al., "Volatile Flavor Compounds Formed in a Interspecific Hybrid between Onion and Garlic", Journal of Agricultural and Food Chemistry, 1993, pp. 1808-1810, vol. 41:10.
Yanagino et al., "Production and characterization of an interspecific hybrid between leek and garlic", Theoretical and Applied Genetics, 2003, pp. 1-5, vol. 107:1.

* cited by examiner

*Primary Examiner* — Cathy Kingdon Worley
(74) *Attorney, Agent, or Firm* — The Webb Law Firm

(57) ABSTRACT

The present invention relates to a hybrid between a leek and a garlic plant. More specifically, the invention relates to an interspecific hybrid plants resulting from a cross between an *Allium ampeloprasum* plant and an *Allium sativum* plant. Specifically, the present invention relates to Interspecific hybrid plants derived from a cross between an *Allium ampeloprasum* plant and an *Allium sativum* plant, wherein the hybrid plants are capable of producing seed and contains nuclear genomic material derived from both said *Allium ampeloprasum* plant and said *Allium sativum* plant, and further wherein the interspecific hybrid plants contain at least 250 mg/kg of allicin when determined in the white part of the leaf sheet of the plants and furthermore wherein the interspecific hybrid plants are obtainable, obtained or derived, from an interspecific hybrid plant as deposited under accession number NCIMB 42564.

7 Claims, 1 Drawing Sheet
Specification includes a Sequence Listing.

| 1 | alliin | ![alliin structure: H2C=CH-CH2-S(=O)-CH2-CH(NH2)-COOH, L-configuration] |
|---|---|---|
| 2 | allysulfenic acid (2-propenesulfenic acid) | CH₂=CH-CH₂-SOH |
| 3 | allicin | allyl-S(=O)-S-allyl |
| 4 | diallyl disulfide (di-2-propenyl disulfide) | allyl-S-S-allyl |
| 5 | Diallyl trisulfide | H₂C=CH-CH₂-S-S-S-CH₂-CH=CH₂ |
| 6 | propenyl methyl disulfide (trans methyl 1-propenyl disulfide) | H₃C-S-S-CH=CH-CH₃ |
| 7 | methyl allyl disulfide (methyl-2-propenyl disulfide) | H₂C=CH-CH₂-S-S-CH₃ |
| 8 | 1,2-vinyldithiin and 1,3-vinyldithiin | 1,2-vinyldithiin + 1,3-vinyldithiin |
| 9 | ajoene | allyl-S(=O)-CH₂-CH=CH-S-S-allyl |
| 10 | allyl methyl sulfide | CH₂=CH-CH₂-S-CH₃ |

SEQUENCE LISTING

<160> NUMBER OF SEQ ID NOS: 67

<210> SEQ ID NO 1
<211> LENGTH: 201
<212> TYPE: DNA
<213> ORGANISM: Allium

<400> SEQUENCE: 1

```
tgaaaccaaa tagtattctt ggactctccc atggattcct tttaggccac ctgcagtcgc    60
ttggccttga ttttcctaag aacatcagtg tagttgctgt rtgccccaag ggcatgggcc   120
catcagtaag aaggctctat gtccaaggaa aggaagtcaa tggtgctggc attaatgcta   180
gctttgctgt tcaccaggat g                                             201
```

<210> SEQ ID NO 2
<211> LENGTH: 201
<212> TYPE: DNA
<213> ORGANISM: Allium

<400> SEQUENCE: 2

```
cctgctccct ctgtgcctgc atatcccgtt cattcttttc ggcaagtgct ttggccgccc    60
tctctgatgt tctttggtgc ctttcgagtc tagctcttct ycgttcttcg gtttctcctt   120
caacttcttg aaagttccca gatgatgagc cacctccaaa aatagaggtc aggtcatcaa   180
caatatttgt tgtggaagat g                                             201
```

<210> SEQ ID NO 3
<211> LENGTH: 201
<212> TYPE: DNA
<213> ORGANISM: Allium

<400> SEQUENCE: 3

```
aagagaaaac gggctcctta caagaccctt gttcgaccat actgtaccag actggctttg    60
ccttgccaac tgagatctcc tgaaatccaa gcccaagaat kccatcaaac ttggctacca   120
ggaaagtcag accaggctct ggtggcttt caataaattc ctgattttc acaacaaggt    180
cccctaattt gacagaatct t                                             201
```

<210> SEQ ID NO 4
<211> LENGTH: 201
<212> TYPE: DNA
<213> ORGANISM: Allium

<400> SEQUENCE: 4

```
ttttaccacg gtattccttg atcataacca catgattttc attccctctg ctctcttctt    60
tctgctcaat agaagatatg attctccaag aagcacggcg ygccccaata acatttttgt   120
atgcaactga aaggaggttc ctctcttcta cagtaagttc ttcagcatca actgattttg   180
ctacctttc catgaactca a                                              201
```

<210> SEQ ID NO 5
<211> LENGTH: 201
<212> TYPE: DNA
<213> ORGANISM: Allium

<400> SEQUENCE: 5

```
acccrctmmt cggattctgg cgccacattg gcacctccca gtccttgrtc ttcttcgaat    60
ggggccctga cygcatcacy ggrtcccgca ttgtcccgac yaaagaggck racagttatg   120
gagttgttaa agttccttc ttgtggctag sgatatcaaa ggaaggagag gcggtgagtt   180
attggttgga ggaagaggat c                                             201
```

<210> SEQ ID NO 6
<211> LENGTH: 201
<212> TYPE: DNA
<213> ORGANISM: Allium

-continued

<400> SEQUENCE: 6

```
caagcacgaa aacaagctcc ttctcatccg gaaacttcag tctcattatc tcaaatggat    60
cgtagcttct taccagaacg aaaccaccaa gaatagcagg rgcgatgtta tctgcatggt   120
aaccactaac cctcttctct gattccaatc ctgcgaggat aaggtcatca tcatccaaaa   180
tatttccaaa gaaagcattg a                                             201
```

<210> SEQ ID NO 7
<211> LENGTH: 200
<212> TYPE: DNA
<213> ORGANISM: Allium

<400> SEQUENCE: 7

```
aagccatyra gaaaatcttr ayysrtaaca gtaaaggaat yaactrtcar atyywrtcra    60
atcyagaatt tcwmgcagaa ggcactrcaa ttgaagattt rttcaarcca gatcrtgtac   120
tgayyggygg acgtgaaack cycgamrggc araaggcrkt tmragcrctt aaagcggtgt   180
atgctaattg ggtgcctgaa                                               200
```

<210> SEQ ID NO 8
<211> LENGTH: 201
<212> TYPE: DNA
<213> ORGANISM: Allium

<400> SEQUENCE: 8

```
tgctggttgg gcagataaga tacatgggct tatagtcccg gccgatgggc cccatcacgt    60
tcaggttctg tacgaaccaa ttggtgttgc agggcaaatc rttccttgga atttccctct   120
tcttatgttt gcttggaaag ttggtccagc tttagcaact ggaaacgttg ttgtacttaa   180
gactgcagaa cagaccccctt t                                            201
```

<210> SEQ ID NO 9
<211> LENGTH: 201
<212> TYPE: DNA
<213> ORGANISM: Allium

<400> SEQUENCE: 9

```
acctggctaa gtgcgcagtg gaaaacaagc gtgtcttttc ccttcaccgc ctgcaaaagc    60
tgaggcatct tctcatgaaa cgattcgcta gcgtagtgat ragatcctgc tatatgcgca   120
tcataactcc tctcgtcgtc tctgacgtcg attatggcga ctctcgcagt tctattgagt   180
aagattagtt gggatgggga a                                             201
```

<210> SEQ ID NO 10
<211> LENGTH: 164
<212> TYPE: DNA
<213> ORGANISM: Allium

<400> SEQUENCE: 10

```
attacacaga tatgagtaaa ttgtatgaga agtacaagga tcaaggattg gagatccttg    60
cttttccttg caaccagttt aactcacaag agccaggaac ygatgaggag attgtgaatt   120
ttgtttgcac acgcttcaag gctgaatatc ccatctttag caag                    164
```

<210> SEQ ID NO 11
<211> LENGTH: 201
<212> TYPE: DNA
<213> ORGANISM: Allium

<400> SEQUENCE: 11

```
ttgctcgatc aacaagaaga atggtcagaa acaccacata gaaataaggt agaaaatgat    60
caaaaagtgc cggcacactc aacagaatg cagcagatat ytctggtgcg tagtggaagt   120
ggcgtgcaag accccaccat ccagaggtca aagaagact ggttttttgtt tccccttttg   180
tggtcgtata agaggcaact a                                             201
```

<210> SEQ ID NO 12
<211> LENGTH: 201
<212> TYPE: DNA
<213> ORGANISM: Allium

<400> SEQUENCE: 12

```
gaccagctgc agacatgaat cctagagcct cgtctactct atgcgctaac tccaggtacc    60
tatccccttg ctcgctgtgc tgtgtaaaat caagattcca rtgagtaacc cgctgcatgg   120
cagcataacc tccagtggca aatgccctca aaagattaag agtagcagca gcctgacagt   180
atgcacgaac cattctatgc g                                             201
```

<210> SEQ ID NO 13
<211> LENGTH: 201
<212> TYPE: DNA
<213> ORGANISM: Allium

<400> SEQUENCE: 13

```
caattagtgg cccgaaacgt ttaatgaaag atctatatgc cggcaataaa acttcagcaa    60
cagcaagcct caaagactca cgtaactctg ggtcaggtac ygcccactga gattgccttt   120
gatgaagctc ctcaaattgc atgttgaatg tcttgagcct ctcttttatg gcagctctag   180
aaacaccgct gctgtttcca c                                             201
```

<210> SEQ ID NO 14
<211> LENGTH: 201
<212> TYPE: DNA
<213> ORGANISM: Allium

<400> SEQUENCE: 14

```
tgacggaggc aaacctcatg ttatcagagg acaaagacct ttttgcagga aaaggagac     60
tatccaaatt gaggcgcaga gcatgaaata tcatagggaa saccaacata agatgaaggg   120
cgtagctcac tcgaacaatg tcgctaaaaa tatgtgaaca tgggattcca agatcggtgt   180
caaagtttgc aaggacatca t                                             201
```

<210> SEQ ID NO 15
<211> LENGTH: 178
<212> TYPE: DNA
<213> ORGANISM: Allium

<400> SEQUENCE: 15

```
ctcggtagtc atactcgtcg aagtacgctc ttctctgctc tttcgacagc ttctgtagct    60
gcgatttttt caatggcttg aaaggtggga gagaatcata ytcatcttct tcttcaaaat   120
catcaaaatc gaactcatcg agatcaatat cggagtcgac gccattatcg ccttgttc    178
```

<210> SEQ ID NO 16
<211> LENGTH: 201
<212> TYPE: DNA
<213> ORGANISM: Allium

<400> SEQUENCE: 16

```
ttcttcaaat accctcaaaa taattgatct gagctaacag atgacaggag atcgacgaat    60
tggagtagcg gtggacttct cctcatgcag caaagcggcg ytgaggtggg cgatcgaaaa   120
tctggcgcgt gatggagacc atctgatttt aatcaacgtt caaaagaag ggttttatga   180 aactggcgag atgcaactat g                                             201
```

<210> SEQ ID NO 17
<211> LENGTH: 201
<212> TYPE: DNA
<213> ORGANISM: Allium

<400> SEQUENCE: 17

```
atctggggat ctctggcctt acattctgac gaacaacagc agaagtgagt tcggcaaaag    60
aaagattagg atatggcata tcacaacaat aaatctccca yaggcaaatt ccaaagctgt   120
atacatcaca tcttctattg tatggttttc cttcgagcac ctcaggagcc atatagccaa   180
gagtaccagt ttcaccagtc a                                             201
```

<210> SEQ ID NO 18
<211> LENGTH: 201
<212> TYPE: DNA
<213> ORGANISM: Allium

<400> SEQUENCE: 18

```
tctgtttctt gttaaggatg tcttttgtga aggagaagta agccatgtca ggtctgcccc    60
atggtccata tacagtaaaa aaacgtaagc ctgttatgga wagtccgtaa atgtggttgt   120
acgtgtgagc aatttcttct cctgcttttt tagttgcagc gtacaaggag gcgggctgat   180
cagtacggtc catttcagag a                                             201
```

<210> SEQ ID NO 19
<211> LENGTH: 201
<212> TYPE: DNA
<213> ORGANISM: Allium

<400> SEQUENCE: 19

```
tacccaagtg ctggttattc aatatcataa ccttgacagg caatttctca atcctaatca    60
tagccaattc ttgaatattc ataagaaaac taccatcacc rtcaatatca atcacagtta   120
cacctgggtt tcctacagct gctccagcag cagcaggcaa tccaaatccc atagctccta   180
atccagctga agtcagccat t                                             201
```

<210> SEQ ID NO 20
<211> LENGTH: 201
<212> TYPE: DNA
<213> ORGANISM: Allium

<400> SEQUENCE: 20

```
accgcccaat atcaagtgat ctcccaactg ctccagactt ataaccttc acaaaatttc     60 tagcaccggg atcaacttct cccaaatttt gcatagtact ygaagactca tcaatagatc   120
cataaattga gttctgaata tatggagaag catatggaac attggatgcg ccattatcaa   180
tggaatttga gttcatcaaa t                                             201
```

<210> SEQ ID NO 21
<211> LENGTH: 176
<212> TYPE: DNA
<213> ORGANISM: Allium

<400> SEQUENCE: 21

| catccacatg | cagaacaaaa | ggctcaaamy | gtacaccggc | aactacgacc | agtacgtcca | 60 |
| racccgcgcc | gagctygagg | aaaaccaaat | gaagcagtac | cgmtgggagc | aggagcrgat | 120 |
| cgccaacatg | aargartaca | tygcccgctt | cggccayggg | tcygccaaac | tggccc | 176 |

<210> SEQ ID NO 22
<211> LENGTH: 201
<212> TYPE: DNA
<213> ORGANISM: Allium

<400> SEQUENCE: 22

| gcgacaggtt | caatgggaat | gaagataaag | caccatggga | gctttatgat | aaagctcaat | 60 |
| cattggtaca | aacggctcag | cattctgcca | gtgattatcc | sttctcactt | aggcgcgagt | 120 |
| ctttatattt | ggatcatgac | cctcattcgg | atccacaagc | ccagcgtctt | gggctttcgt | 180 |
| cgctttatcg | atcagaaaca | c | | | | 201 |

<210> SEQ ID NO 23
<211> LENGTH: 201
<212> TYPE: DNA
<213> ORGANISM: Allium

<400> SEQUENCE: 23

| ctgtctacga | tttataactc | tgccaccata | tgcaccctct | ctaagcagcc | aacgcaacag | 60 |
| atagtacccc | aaaaaccagt | ccaaaaatag | tcatttcctt | yctcgctgac | ccactcgtat | 120 |
| cgtcagaggc | gccagggcca | ggagacacag | cstcagatcc | agtcggagcc | atcgtcggag | 180 |
| acgatacaga | actgaccgtc | g | | | | 201 |

<210> SEQ ID NO 24
<211> LENGTH: 201
<212> TYPE: DNA
<213> ORGANISM: Allium

<400> SEQUENCE: 24

| tgtcacctga | ggatgcagat | gtacatattg | tacttggtgt | attatacaac | ttatccaggg | 60 |
| aatatgataa | agcaatacag | tcatttgaaa | atgcactgaa | rctcaggcca | cgcgattact | 120 |
| ctttatggaa | caagcttggt | gcaaccaaag | craacagtgt | tcaaagttca | gaagcaatat | 180 |
| tagcttatca | gcaggcacta | g | | | | 201 |

<210> SEQ ID NO 25
<211> LENGTH: 201
<212> TYPE: DNA
<213> ORGANISM: Allium

<400> SEQUENCE: 25

| ccttctcacc | tttgcttgta | catactggtg | cagttaactg | aagtttcgct | agatcgtttt | 60 |
| tcactgcaat | gactttagct | ccagttgaca | tggaacctat | rttaagcatc | agaatttccg | 120 |
| cttttgttag | cttcgatact | tttccttgct | tttctgcacc | ttttgttctt | actcccaata | 180 |
| gccttctcag | taaaaagaag | t | | | | 201 |

<210> SEQ ID NO 26
<211> LENGTH: 201
<212> TYPE: DNA
<213> ORGANISM: Allium

<400> SEQUENCE: 26

```
ctctgtgcct gctgctgtgg tgatcgccat gtctatctct atcatctcta tacctctctc    60
tttctcctct atctctatcc ctactccttt ccctctctct rtcatagtct ctacttcgtt   120
cccttcctct atcctctcct ctatgccttc tttcaaccat atcttgccct ccttcgaaat   180
ctttctctct ttcatgcctt c                                             201

<210> SEQ ID NO 27
<211> LENGTH: 201
<212> TYPE: DNA
<213> ORGANISM: Allium

<400> SEQUENCE: 27
acttaatgta gaacctagaa ccgctgacag agagcttagt ctctagaaga tccgcaagcg    60
ctgagcttaa ttttccattc acaccaggac cgaggccacc rattgatata acctctccat   120
atgcagctgg ctcttcgctt ccaccaaata ctataggcac tccaccattg acgatcacca   180
taacatacga ttcgggcttg c                                             201

<210> SEQ ID NO 28
<211> LENGTH: 201
<212> TYPE: DNA
<213> ORGANISM: Allium

<400> SEQUENCE: 28
tggcaggacc aaccctcatt tgccgtgtag aacagtactg accatccatt tcagtcattg    60
cacgagtttg ttcatttaaa tcggcaaact taacaaaccc rtagcccttg gaacgccctg   120
tgattctatc agtaactatc ttagctcctc taaccgaagg ataatggctt ttaaaagtct   180
cttgtaatac ataatcagtg a                                             201

<210> SEQ ID NO 29
<211> LENGTH: 201
<212> TYPE: DNA
<213> ORGANISM: Allium

<400> SEQUENCE: 29
caaaaggtaa gggtatttcg tcgtcggcgc taccctacaa gagaaccccca cctagctggg   60 tcaaaaccaa gcccgaagag gtccaggagc aaatatgtaa rtttgcaaag aagggtctaa   120
caccatctca aattggtgtt attctccgtg attcatctgg tattcctcag gttaagagtg   180
tcactggaag caagattctw c                                             201

<210> SEQ ID NO 30
<211> LENGTH: 201
<212> TYPE: DNA
<213> ORGANISM: Allium

<400> SEQUENCE: 30
ctaccgttct tccatcgatc gtatgcttat cattaagaac agtttcaaga accgaaggat    60
ccgcaaaaac aacaaatccg aaacctctcg gtttaccagt wagcttgtct cgcataatta   120
cagtttgaag aacttcgcca taattactaa aatactgttt cattttatct tcgtcggttt   180
cccatgagat cccgcctatg a                                             201

<210> SEQ ID NO 31
<211> LENGTH: 201
<212> TYPE: DNA
<213> ORGANISM: Allium
```

-continued

<400> SEQUENCE: 31

```
gcacgttgag gatccactgg gggaaaaaac atggcatgcg gtacttgagg tggtacaaaa      60
ggcatgcccc taatagcctc tggatattgt tgctgtgcga sgtaataaat tggagaagga     120
aactcagcat atcccatagc actaccagca agaggatggg gcaatggagg tggtggaggc     180
ataaaatgct gtggtctatg a                                               201
```

<210> SEQ ID NO 32
<211> LENGTH: 201
<212> TYPE: DNA
<213> ORGANISM: Allium

<400> SEQUENCE: 32

```
atccaaactg acaaaggggg aaattctaat gcttaacatt ggttcaatgt caactggagc      60
taaagtgata gcagtgaaga acgacttagc taagctacaa ytgacagcac ctgtatgcac     120
aagcaaaggg gagaaagttg ctctcagcag aagagtcgaa aaacattggc ggcttattgg     180
ttggggtcag atccaggccg g                                               201
```

<210> SEQ ID NO 33
<211> LENGTH: 201
<212> TYPE: DNA
<213> ORGANISM: Allium

<400> SEQUENCE: 33

```
caaagcctct ggatctcccg gtatctctat cgatgacaac tctagcatcc gttacttttc      60
cttgttcact aaatagagtt tcaagggcaa gattgtcaac ycccatgat aagttaccaa      120
catatagtct gctgccagct tcaaagttag cagcattgcc gctgccaccg cttctgaaac     180
ttctgggtgc acgctcctct c                                               201
```

<210> SEQ ID NO 34
<211> LENGTH: 201
<212> TYPE: DNA
<213> ORGANISM: Allium

<400> SEQUENCE: 34

```
tcgggctttc ttcagccaag caattctgtc tgcttggtat tattcttgtt atcaccgagt      60
tgtttgggac gcctacgaaa ttcatcttca ctgcttccac raaggcctg atgtcgaact     120
ctgcatttcc catttcgtca tcagcactga acaagtcttt gtcgtaaact tccacactaa     180
ctggtagtga aggatcttca a                                               201
```

<210> SEQ ID NO 35
<211> LENGTH: 201
<212> TYPE: DNA
<213> ORGANISM: Allium

<400> SEQUENCE: 35

```
caattttttgc tatggttctt agtggatttt atgtattgag cccgatcgac attattcctg      60
aaggtttact gggatttgtt ggcttgcttg atgattttct rattgtacta gttgttttc      120
tccacctagc tactctatat cggtctttgc ttcttaaccg ccatggagga ggatattgat     180
tactagctat ttctcaaccg t                                               201
```

<210> SEQ ID NO 36
<211> LENGTH: 201
<212> TYPE: DNA
<213> ORGANISM: Allium

```
<400> SEQUENCE: 36
acaaaaacac ccatgattct ggcatggtat caccaaaatg cccatttgga tatgattctc      60
atactttcaa attaggccct ttaagctgca tgatttgcaa rgcattgctt taccaaagta     120
gcaaatgtat gccttgctct cataaatttt gcaaagcatg tatatcccga tttagagatt     180
gtccactttg tggtgccgac a                                               201

<210> SEQ ID NO 37
<211> LENGTH: 201
<212> TYPE: DNA
<213> ORGANISM: Allium

<400> SEQUENCE: 37
tttcagctat cttcaatcta attcctatta cgatggcaga tgaggttgcg gtcgagacag      60
tcgctccggc tctcggagaa cccatggata ttatgactgc wctacaagtt gtgttaaaga     120
aatcactggc tcatgatggc cttgtacgtg ggctccatga agctgctaag gcaattgaga     180
agcatgctgc acagctatgt a                                               201

<210> SEQ ID NO 38
<211> LENGTH: 201
<212> TYPE: DNA
<213> ORGANISM: Allium

<400> SEQUENCE: 38
caatgaacga ttcatatcac agaagagttt ggaacataat gagcttcttc aagtcaaaaa      60
gtccctgagc ttaaagcaaa gactaaatttt tggtcacaaa ytaaacagtg ttaaaacaat    120
taaagttgag gctctgaatc cagttaatgt ggatccacgt aggggcaaac attcggtggc     180
agttaacaat catttgaatg g                                               201

<210> SEQ ID NO 39
<211> LENGTH: 201
<212> TYPE: DNA
<213> ORGANISM: Allium

<400> SEQUENCE: 39
tcatgaccat ttcttccagc atgaagtgtg ctttctcaag atggaacatt atatcaagtt      60
cacacacatt gccaaaatga cggtccatag tctccaccaa yagatgtata aattccagaa     120
ttgctaattc atttcatca ttgtccaccc caaccaagaa aaatagtgaa gcatagcgcc      180
tgtacacaac tttgtaattc c                                               201

<210> SEQ ID NO 40
<211> LENGTH: 201
<212> TYPE: DNA
<213> ORGANISM: Allium

<400> SEQUENCE: 40
acacaaggaa gcttgcagag gaaacagaga acctgaccca tgagagagtt ccaagtgaac      60
tgaagaagaa catcatacaa gctcgaacag ataaaaagct yacacagtcc caacttgctc     120
agcttatcaa tgagaagccg cagatcatac aggaatacga gtcaggaaaa gctattccaa     180
atcagcagat aatatccaaa c                                               201

<210> SEQ ID NO 41
<211> LENGTH: 201
<212> TYPE: DNA
```

<213> ORGANISM: Allium

<400> SEQUENCE: 41

| tcaacgaata caagctgcca gcctgatctc aagggtcgt ccaactgacc ttcaaggcca | 60 |
| aaaagacgcc ccaactcact cctaagttcc gggtaactcg waaattttgt tatatccaac | 120 |
| gacctcccaa aggacccaga tttgtatacc tttacaaacg ttccactttg ttggttaact | 180 |
| tgatccccac catcagtaga a | 201 |

<210> SEQ ID NO 42
<211> LENGTH: 201
<212> TYPE: DNA
<213> ORGANISM: Allium

<400> SEQUENCE: 42

| aaatgggaca ggcagagtca aaatctaaag atgttgaaga agaattgatg catggcctta | 60 |
| atagagtttc tgagctttct caagaattag aagcattcaa rgcaagatca gagagtttag | 120 |
| aatatgttgt gcaggcagcg agtgaaaagg agaaagagtt aacaaatacg ttgaatgaag | 180 |
| ttgtggaaga aaagaagaaa t | 201 |

<210> SEQ ID NO 43
<211> LENGTH: 180
<212> TYPE: DNA
<213> ORGANISM: Allium

<400> SEQUENCE: 43

| catcatctaa ctcatagtac acctttccag aacacaagac caacctacta atgccctctt | 60 |
| caacatcttt atggtcattc tgatctttga ttaaacgctt raaacgagtt ccttgcttat | 120 |
| cgaaccctgg atggccaaca acatcatcaa attctgacaa atttgactta cagtctttgt | 180 |

<210> SEQ ID NO 44
<211> LENGTH: 201
<212> TYPE: DNA
<213> ORGANISM: Allium

<400> SEQUENCE: 44

| gaagtcgatc cccgaggact ggaactgctt gccatattat tcatgggagc gaaagctcta | 60 |
| tccctcattc ttctttccct gtcatattca aatttatctc kaatttgccc aaccttgtcc | 120 |
| cagttatcat tttgcctatt cccaccacct ccaaataatt gatccttatt tggttcagga | 180 |
| tgagtccggc tcctcctgta t | 201 |

<210> SEQ ID NO 45
<211> LENGTH: 201
<212> TYPE: DNA
<213> ORGANISM: Allium

<400> SEQUENCE: 45

| ctgatggagt tacaccagaa aaattgagaa ctctttttga gtgtcatgga gaagtcacca | 60 |
| aaattgtttt accaccatca aaaactggat taaagaagcg rgattttggg tttatccatt | 120 |
| ttgctgagag atccagtgct ttaaaggcag taaaagtagc taaatatgaa atagagggac | 180 |
| aacctataga agttgtatta g | 201 |

<210> SEQ ID NO 46
<211> LENGTH: 201
<212> TYPE: DNA
<213> ORGANISM: Allium

<400> SEQUENCE: 46

```
ctactttcac attgccaata aaaactccag ataataggca agtatgagat cttgcattgc    60
ttgggacagt atcagttccc tcacagggtt gcatgccaag watattaatg acagcactga   120
cagccatggc caagttatct ctggtaccaa gtccgtattc atcaacacgc tcagtatcag   180
ggtccatact gtcccatgca t                                             201
```

<210> SEQ ID NO 47
<211> LENGTH: 201
<212> TYPE: DNA
<213> ORGANISM: Allium
<400> SEQUENCE: 47

```
ctaatgtcag ttgggaggat attggtggtc ttgaaaatgt aagagggaa ctacaagaga     60 ctgttcaata tcctgtggaa catcctgaga aatttgagaa rttcggcatg caccttcta    120 aaggagtctt gttctatgga cctcctggtt gtgggaaaac tttgctggct aaggcaatag   180
ctaatgaatg ccaagcaaac t                                             201
```

<210> SEQ ID NO 48
<211> LENGTH: 201
<212> TYPE: DNA
<213> ORGANISM: Allium
<400> SEQUENCE: 48

```
tcacaatgtg aatatatgta aaaactactc aatattttaa gtaagctagt acctcaagaa    60
gagaagcagc aaactccatc tgaagttcct cgtcgatagt raagaaaaga ggcacgtgca   120
caaagagaga tttaatttta tgctcctcag caaatcgaag agagtggtag taaatgtaat   180
tacatacaaa tcttccagca t                                             201
```

<210> SEQ ID NO 49
<211> LENGTH: 201
<212> TYPE: DNA
<213> ORGANISM: Allium
<400> SEQUENCE: 49

```
acgtttcaag agattccagg tgcctgatta cagcaagtgc cgatcaaact gtaaagctat    60
ggaatgttca gacgggaaca ccgacatatt catttaagtt ygattcacct gctaggtccg   120
tacagttttc tcttggtgat aagcttgctg ttattaccgc agatcctttt atgggccatc   180
cttctactat tcaagttaag c                                             201
```

<210> SEQ ID NO 50
<211> LENGTH: 201
<212> TYPE: DNA
<213> ORGANISM: Allium
<400> SEQUENCE: 50

```
tctacgactg aataggcttg atcttgaagt ggagcgagat cagtgagaaa acaaagcact    60
tcaaatcctg aacaagataa tagaaaatac gcagcccttc rggatcttta ctactttgca   120
catccacaag cgacccaatc tttgaagtcg tgaatgaaat atgctcattg cccatcacaa   180
tctccagctc ttgcctccct a                                             201
```

<210> SEQ ID NO 51
<211> LENGTH: 201
<212> TYPE: DNA

<213> ORGANISM: Allium

<400> SEQUENCE: 51

| atatccttgt | ttaatttcag | gaacatcagt | aatatcgcca | atggcaaaaa | cattcttcca | 60 |
| cccttaact | ctgaaactct | catcaaccat | tagttgccct | wttttgttta | tacagtcctt | 120 |
| caacatagtc | tcctgaagcc | atgatgaacc | taatgttttc | ccaacacaga | gaaatttagc | 180 |
| atccgctgta | attttttcac | c | | | | 201 |

<210> SEQ ID NO 52
<211> LENGTH: 201
<212> TYPE: DNA
<213> ORGANISM: Allium

<400> SEQUENCE: 52

| ttccaggata | tgcatggaca | attacaaatt | gtgcaacatg | tgagtccaac | atgggttggc | 60 |
| tatttacagc | tacgaaaaag | aatttgctac | caagatcgtt | ytggggaatc | cgtagctctc | 120 |
| aagttacaga | tgatacctca | attttggaca | aggaactaaa | gtgaaaacac | gtaatagttt | 180 |
| acctataaca | atatcttgat | c | | | | 201 |

<210> SEQ ID NO 53
<211> LENGTH: 201
<212> TYPE: DNA
<213> ORGANISM: Allium

<400> SEQUENCE: 53

| tccaagaacc | catttgggtg | caggaaggat | ggatttactc | ctgaaacaaa | tggagctccc | 60 |
| ccagcaatca | attagcagca | gtgccattga | aggatgtaat | wttttataca | tgcaccatga | 120 |
| agaagagaac | tagattatgt | cgacatgact | tgattcatgt | tattgcattt | gatcatcttt | 180 |
| catcttcatt | catgttacct | a | | | | 201 |

<210> SEQ ID NO 54
<211> LENGTH: 161
<212> TYPE: DNA
<213> ORGANISM: Allium

<400> SEQUENCE: 54

| gaaatggagc | taacctcgct | aacattcgta | atttatctgg | agccgacatc | gaaattgtcg | 60 |
| attcacgttc | atcaagatat | gagcacattg | ctcagataac | sgggactcat | gagcagaagc | 120 |
| gttcagcaga | aaatatgatt | caggctttta | tcttgtcaac | t | | 161 |

<210> SEQ ID NO 55
<211> LENGTH: 175
<212> TYPE: DNA
<213> ORGANISM: Allium

<400> SEQUENCE: 55

| ggacgcacgt | tggaatcggt | caggttaact | ttgcccttte | cagtagtgaa | attgctgagt | 60 |
| ccgaggtggt | atcggagttc | ttcttcagat | gcagcatatg | kgatatcgat | tttgttccca | 120 |
| agaatgagga | atgggacggt | cgccagtgat | tcatcagaaa | gaagtgcatc | gagct | 175 |

<210> SEQ ID NO 56
<211> LENGTH: 201
<212> TYPE: DNA
<213> ORGANISM: Allium

<400> SEQUENCE: 56

```
atgggaagag cttattaaac aatgctttcg ccagcctgaa atggtaggga tgttgcttga      60
gcacactgta ggtaatctgg atccattata tatagtcagt mgagtgccaa atggtctaga     120
aatacctcgg ttaagagacc gccttgtcaa atcatcacc gattatcgaa ctgaaacttc      180
tttaagacat ggatgcaatg a                                               201
```

```
<210> SEQ ID NO 57
<211> LENGTH: 191
<212> TYPE: DNA
<213> ORGANISM: Allium

<400> SEQUENCE: 57
gggtagacca cgaacgcgaa caactggcaa tgatggaggt tgattatcat aggcatatgg      60
aatcgtgtga ggaagatttg aactggaagg wgctccataa taagcaccgg tatccataag     120
atgctgtctc tttaatctcg tatcaagagc accaccgcta tctgcatatt ccgtttgaa      180 atcgccaccg g                                                          191
```

```
<210> SEQ ID NO 58
<211> LENGTH: 201
<212> TYPE: DNA
<213> ORGANISM: Allium

<400> SEQUENCE: 58
tcaagaaaga agtctgaagt gacgctagct gcaccagcac ttcaattgcc ttaagatgtg      60
ctgcacggca tgcctgtatc tgctgacccc ctcgtgcaag rccagtcaaa tcattcgacg     120
attttgaatc gggcaacgaa gaatctaagt aatgttcaaa tttcggaagc ttgactccag     180
ctacattatc ttgacgagaa c                                               201
```

```
<210> SEQ ID NO 59
<211> LENGTH: 197
<212> TYPE: DNA
<213> ORGANISM: Allium

<400> SEQUENCE: 59
tgggagagaa gtttaccctg atggagtttt atatgcctca aaggaaagcc attattctgt      60
atttaaagca gcaagaatgt acagaatgga atgcgttaaa rttgatactt tgatttctgg     120
tgaaattgac tgcagcgatt ttgaaaagaa actcctcttg aacaaggaca aaccagccat     180
cataaacgtc aatattg                                                    197
```

```
<210> SEQ ID NO 60
<211> LENGTH: 201
<212> TYPE: DNA
<213> ORGANISM: Allium

<400> SEQUENCE: 60
atacacgatc agcaattgcc tttgtttgag cagcaacaac atccattgtt gatccagatt      60
cacgttgctc aagagtttca ccaacacatg caattacctt yaaaccttga gaaagagcat     120
atttaacttt gtccccaaca aactcgttgg attcacctaa taaggctctt ctctctgagt     180
gaccaagaat gacccaagga a                                               201
```

```
<210> SEQ ID NO 61
<211> LENGTH: 201
<212> TYPE: DNA
<213> ORGANISM: Allium
```

```
<400> SEQUENCE: 61
tagttggatc aatgggagga acagatctaa caaatcctct aaacagtctg ggaaatggta      60
acatattggt ctggaagcgc aaagctgaac aatatttagc rgactctgga ataccatata     120
caattataag agctggaggt ttacaggata aagatggagg cataagggaa ttacttatcg     180
gtaaggatga tgagcttctc a                                               201

<210> SEQ ID NO 62
<211> LENGTH: 201
<212> TYPE: DNA
<213> ORGANISM: Allium

<400> SEQUENCE: 62
aacgtgttta tgaaattgga aaacaattta ggaatgaggg gatagatatg acccacaatc      60
ctgaatttac tacatgtgaa ttttatatgg catatgcaga ytacaatgat ttgatggacc     120
taacggaaaa aatgatatcc ggaatggtaa aggagttaac aggtggctat aaaattttgt     180
accatgcaaa tggagttgac c                                               201

<210> SEQ ID NO 63
<211> LENGTH: 181
<212> TYPE: DNA
<213> ORGANISM: Allium

<400> SEQUENCE: 63
taggatcatt atccttcaaa cctgttttta gtacaacggt ctgccctttt gccttctcca      60
tatccttttt caacctatcc atgctctcct ttctacgttc wgtctctaat ctatccttct     120
cagcacgcct tttgtcaagg tcagccttgt agttttccat atactcagta gcactggctt     180
c                                                                     181

<210> SEQ ID NO 64
<211> LENGTH: 201
<212> TYPE: DNA
<213> ORGANISM: Allium

<400> SEQUENCE: 64
tccccactaa ctgttgctca gtcagcggtt cgagttgatc ggctaatagc ttcaagattt      60
cagaggttct aaatcctcct aaccatagga agcacctttc ycaggtgtg gtccacattc      120 cagacagtat atggaaaaca tccattttgg cagccatact tttgagctta aataatttat     180
catagtgcgc catgacacca t                                               201

<210> SEQ ID NO 65
<211> LENGTH: 201
<212> TYPE: DNA
<213> ORGANISM: Allium

<400> SEQUENCE: 65
cccaataaac aaatgcaata acaggtcctt ctctgattaa cttcccatcg agaatcacaa      60
gatccccatc aacccaccta gggtttcgaa aaccaggatc rgctatcctt ccttgtccct     120
tatacctagc aatcacacca aattcttctg gtataatacc cttatgagga agctgatact     180
gtttgcctat ttttgcacgg a                                               201

<210> SEQ ID NO 66
<211> LENGTH: 201
<212> TYPE: DNA
<213> ORGANISM: Allium
```

```
<400> SEQUENCE: 66
tgaaaccaaa tagtattctt ggactctccc atggattcct tttaggccac ctgcagtcgc    60
ttggccttga ttttcctaag aacatcagtg tagttgctgt gtgccccaag ggcatgggcc   120
catcagtaag aaggctctat gtccaaggaa aggaagtcaa tggtgctggc attaatgcta   180
gctttgctgt tcaccaggat g                                             201

<210> SEQ ID NO 67
<211> LENGTH: 201
<212> TYPE: DNA
<213> ORGANISM: Allium

<400> SEQUENCE: 67
tgaaaccaaa tagtattctt ggactctccc atggattcct tttaggccac ctgcagtcgc    60
ttggccttga ttttcctaag aacatcagtg tagttgctgt atgccccaag ggcatgggcc   120
catcagtaag aaggctctat gtccaaggaa aggaagtcaa tggtgctggc attaatgcta   180
gctttgctgt tcaccaggat g                                             201
```

INTERSPECIFIC HYBRID PLANT RESULTING FROM A CROSS BETWEEN AN *ALLIUM AMPELOPRASUM* PLANT WITH AN *ALLIUM SATIVUM* PLANT

CROSS-REFERENCE TO RELATED APPLICATIONS

This application is the United States national phase of International Application No. PCT/EP2018/051085 filed Jan. 17, 2018, and claims priority to European Patent Application No. 17152251.9 filed Jan. 19, 2017, the disclosures of which are hereby incorporated by reference in their entirety.

The Sequence Listing associated with this application is filed in electronic format via EFS-Web and is hereby incorporated by reference into the specification in its entirety. The name of the text file containing the Sequence Listing is 1904733_ST25.txt. The size of the text file is 25,141 bytes, and the text file was created on Feb. 7, 2020.

The present invention relates to a hybrid between a leek and a garlic plant. More specifically, the invention relates to an interspecific hybrid plant resulting from a cross between an *Allium ampeloprasum* plant and an *Allium sativum* plant. The invention further relates to plant parts, seeds, edible parts, pollen, egg cells, protoplasts, callus, cultured cells, cultured tissues, somatic embryos or zygotic embryos of such interspecific hybrid plant, methods for generating such interspecific hybrid plant and use of such interspecific plant to obtain seed.

Leek and garlic both belong to the genus *Allium*, which further includes the economically relevant crops onion, shallot, chives and scallion. The genus is generally referred to as the onion family. Plants within the genus contain characteristic substances derived from cysteine sulfoxides giving these plants their characteristic onion or garlic taste and odor. Many species in the genus are used as food plants, where usually both the bulb and the leaves are edible. *Allium* species are herbaceous perennials. They produce flowers on scapes and grow from solitary or clustered tunicate bulbs. Plants are perennialized by bulbs that reform annually from the base of the old bulb, or are produced on the ends of rhizomes or, in a few species, at the ends of stolons. A small number of species have tuberous roots.

The species *Allium ampeloprasum* is also known as wild leek or leek, and can be further subdivided in several varieties such as elephant garlic (*A. ampeloprasum* var. *ampeloprasum*), leek (*A. ampeloprasum* var. *porrum*; also known as *Allium porrum*), kurrat (*A. ampeloprasum* var. *kurrat*), pearl onion (*A. ampeloprasum* var. *sectivum*), Persian leek (*A. ampeloprasum* ssp. *persicum*) and Guernsey leek (*A. ampeloprasum* var. *bulbiferum*). Unlike most species in the onion family, leek produces a long cylinder of leaf sheets which is edible. Leek is commercially grown for its mild onion like flavor, and can be consumed raw or cooked, its most common use is as flavoring in stock. Leek plants produce scapes of up to 180 cm tall bearing an umbel of up to 500 flowers.

Garlic (*Allium sativum*) is a bulbous plant grown for use as food flavoring and use in traditional medicine. Two species of *Allium sativum* are known: *A. sativum* var. *ophioscorodon* (hard necked garlic), and *A. sativum* var. *sativum* (soft-necked garlic). Hundreds of varieties are known which can be divided in ten variety groups. Although the entire plant is edible, generally the bulb is consumed. The bulb usually consists of numerous fleshy sections called cloves, with the exception of single clove garlic types. Flowers are generally absent in garlic plants, however bulbils are formed at the tip of the scape. Garlic plants may very occasionally produce flowers, allowing sexual reproduction in a breeding program. However for the purpose of horticultural production the occurrence of flowers in garlic plants, and thus ability to grow seed is so low that the plant is essentially regarded as sterile. Therefore, typically garlic is propagated asexually using cloves, although the bulbils can also be used for growing new plants. Essentially all cultivated garlic is propagated asexually by planting individual cloves or bulbils.

Most types of garlic plants consist of a bulb above the basal plate which is compartmentalized in cloves; cloves generally form in the first year of plant development. Leek stems, may be completely straight or more bulbous. When grown longer clove-like structures may develop in leek as well.

In food flavoring, garlic is generally used because of its typical pungent flavor and odor which is mostly derived from alliin present in garlic Alliin is a sulfoxide compound, giving rise to the specific odor and taste associated with garlic through a series of chemical reactions. When fresh garlic is damaged, for example through crushing or chopping, alliin is converted by the enzyme alliinase into allylsulfenic acid (also known as 2-propenesulfenic acid) and pyruvic acid. Allylsulfenic acid subsequently forms allicin by dimerization. Allicin, which has been suggested to have antibacterial activity, is an unstable organosulfur compound and quickly reacts to form a variety of sulfur containing compounds. Some of the compounds formed in this reaction are diallyl disulfide (also known as di-2-propenyl disulfide), diallyl trisulfide (also known as di-2-propenyl trisulfide), propenyl methyl disulfide (also known as trans methyl 1-propenyl disulfide), vinyldithiins (1,2-vinyldithiin and 1,3-vinyldithiin) and ajoene. These compounds can give rise to further metabolites such as allyl methyl sulfide (see FIG. 1 for an overview of these compounds and their chemical formulae). Allicin, diallyl disulfide, diallyl trisulfide, propenyl methyl disulfide, vinyldithiins, ajoene and methyl sulfide are known to contribute to the typical garlic odor and/or taste.

For culturing of different leek or garlic varieties as well as developing new varieties, it is highly advantageous to have substantially uniform F1 hybrids available. One way of achieving this is by using or generating cytoplasmic male sterile (CMS) plants. Male sterility in plants arises when a plant does not produce (functional) pollen. Such plants are known as female. Male sterility can be nuclear, when the underlying cause is encoded by the genomic DNA (NMS), or cytoplasmic if the cause is encoded by the mitochondrial and/or chloroplast DNA (CMS). NMS is also referred to as genic male sterility or genetic male sterility.

CMS parent lines are advantageous for breeding purposes, as they provide control over the genetic progeny. In principle it can be assumed that in sexual reproduction half of the progeny's nuclear genetic material originates from the male parent line which is male fertile and the other half originates from the male sterile female parent line. As no seed is harvested from the male fertile line, this line may be female fertile as well (and thus able to self-pollinate). In plants that are male and female fertile, self-pollination occurs in parallel with crossing between plants, resulting in a mixed population of self-pollinated and crossed plants. Therefore, CMS parent lines allow the development of F1 hybrids, which in general have the advantage of better emergence, higher yield, more vigor and/or high uniformity.

Cytoplasmic male sterile (CMS) plants have been described for both *Allium ampeloprasum* and *Allium sativum* in WO 2010/007059, where CMS *Allium ampeloprasum* plants were obtained by crossing of *Allium ampeloprasum* with a naturally occurring CMS *Allium sativum* variety and subsequent backcrossing with *Allium ampeloprasum*. It is to be understood that CMS plants (female plants) can still produce (fertilized) seeds, however not through self-pollination.

In modern horticulture a constant need exists to introduce new varieties and species of edible plants. Reasons for introducing new varieties and species, amongst other, may be to improve disease resistance, increase yield or nutritional content, meet changing market demands or adapt crops so they are capable of growing in different climates. New varieties are traditionally obtained by breeding programs. New species may be obtained by crossing different species to generate an interspecific hybrid.

Leek and garlic are related species within the subspecies *Allium*, and it was found that interspecific hybridization is possible. An advantage of such a hybrid is that it can be introduced as a new food product. Other possible advantages of generating a leek and garlic hybrid are amongst others introducing desirable traits from garlic into a leek-like plant. Examples of desirable traits are amongst others disease resistance, improved edible part production, improved color, or improved plant growth.

An interspecific hybrid plant of leek and garlic has been described by Yanagine et al. 2003 (Reference 1). The main purpose of this study was introducing disease resistance of leek into a garlic plant. The resulting plant is a hybrid which phenotypically appears to be an intermediate between garlic and leek. Like garlic it produces cloves, although less in number, as opposed to leek which produces a bulb or sometimes two cloves (when not harvested in autumn or winter). This hybrid must be vegetatively propagated and is thus not fit for breeding purposes or commercial seed production.

Generation of a leek and garlic hybrid has further been suggested as a method of introducing cytoplasmic male sterility (CMS) found in certain garlic varieties into leek. Such method has been described in WO 2010/007059, where a cross between CMS *Allium sativum* and *Allium ampeloprasum* and subsequent backcrosses with *Allium ampeloprasum* resulted in a *Allium ampeloprasum* plant with the cytoplasmic male sterility derived from *Allium sativum*.

For the purposes of commercial agriculture and plant breeding a plant which can produce seeds is highly desirable when compared to a plant which requires vegetative propagation. Vegetative propagation poses several drawbacks, such as large volume of bulbs or cloves resulting in high costs for storage and transport. Vegetative propagation further has an increased risk of introducing diseases, as many diseases can be transmitted to progeny through the bulb/cloves, as opposed to much fewer diseases which can survive in seed. Moreover, seed may be treated to remove certain diseases, which is not possible with bulbs or cloves. Lastly, vegetative propagation is undesirable for breeding purposes as plants are identical to the parent and thus cannot give rise to new and improved varieties.

To overcome among others the above drawbacks of the prior art, it is an object of the invention to provide a hybrid between leek and garlic which is capable of producing seeds. It is a further object of the invention to stably introduce the odor and taste of garlic in a leek-like hybrid plant. These objects, among others, are met by the present invention by providing plants and methods as defined in the appended claims.

In a first aspect of the invention is provided an interspecific hybrid plant derived from a cross between an *Allium ampeloprasum* plant and an *Allium sativum* plant, wherein said hybrid plant is capable of producing seed and contains nuclear genomic material derived from both said *Allium ampeloprasum* plant and said *Allium sativum* plant, wherein said interspecific hybrid plant contains at least 250 mg/kg of allicin when determined in the white part of the leaf sheet of the plant and further wherein said interspecific hybrid plant is obtainable from an interspecific hybrid plant as deposited on 21 Mar. 2016 under accession number NCIMB 42564 (National Collections of Industrial, Food and Marine Bacteria (NCIMB), NCIMB Limited, Ferguson Building; Craibstone Estate, Bucksburn Aberdeen, Scotland, AB21 9YA United Kingdom).

In light of the invention the term derived from a cross between an *Allium ampeloprasum* plant and an *Allium sativum* plant should be interpreted as the plant directly obtained from a cross between an *Allium ampeloprasum* plant and an *Allium sativum* plant, as well as all further progeny obtained from this direct cross. Further progeny may be obtained through vegetative propagation, by self-fertilization, by cell fusion, doubled haploid production or by crossing the directly obtained plant with one of the parents, crossing the directly obtained plant with another plant directly obtained from a cross between an *Allium ampeloprasum* plant and an *Allium sativum* plant, crossing the directly obtained plant with a different *Allium ampeloprasum* plant or *Allium sativum* plant, or crossing the directly obtained plant with a different species within the *Allium* genus altogether.

A cross between an *Allium ampeloprasum* plant and an *Allium sativum* plant resulting in an interspecific hybrid encompasses the crossing of *Allium ampeloprasum* with *Allium sativum* and results in a plant harboring genetic elements of both species in its nuclear genome. Such crossing may be achieved by fertilization of the ovules of an *Allium ampeloprasum* plant by pollen of an *Allium sativum* plant, or by fertilization of the ovules of an *Allium sativum* plant by pollen of an *Allium ampeloprasum* plant. It should however be understood that "cross" is not limited to naturally occurring fertilization methods and can also be achieved by other methods known to the skilled person. For the purpose of the invention a cross between an *Allium ampeloprasum* plant and an *Allium sativum* plant should therefore be considered any process resulting in a plant, seed, part of a plant, embryo or somatic cell containing nuclear genomic material of both *Allium ampeloprasum* and *Allium sativum*.

A cross between an *Allium ampeloprasum* plant and an *Allium sativum* plant resulting in an interspecific hybrid encompasses the crossing of *Allium ampeloprasum* with *Allium sativum* resulting in a plant harboring genetic elements of both species in its nuclear genome. The skilled person will appreciate that such hybrid plant not only comprises plants resulting from a direct cross between these plants harboring equal amounts of genetic material from each *Allium ampeloprasum* and *Allium sativum*, but also comprises progeny obtained from this direct cross, resulting in plants which may have unequal distribution of genetic material of *Allium ampeloprasum* and *Allium sativum*. Such plants according to the invention include plants where at least one chromosome or part thereof or one or more genes derived of each species are still present in the plant. Preferably such plant comprises substantially the genome of *Allium ampeloprasum* and in addition comprises one or more chromosomes derived from *Allium sativum*, or a fragment of a chromosome derived from *Allium sativum* or one or more genes derived from *Allium sativum*. Such plant can also encompass plants which largely comprise the genomic material of either *Allium ampeloprasum* or *Allium sativum* while harboring at least one but preferably more genes of the other species. Such chromosome, part of a chromosome or at least one gene can be present individually as a stable chromosome, a stable fragment of a chromosome or be integrated in a chromosome of the other species through homologous recombination or random insertion. Preferably the combination of nuclear genomic material derived from *Allium ampeloprasum* and *Allium sativum* is present in the plant in a stable fashion and as such can be passed along to its progeny when crossed with an *Allium ampeloprasum* plant, an *Allium sativum* plant, a hybrid thereof or a different species within the *Allium genus* capable of crossing with a hybrid plant. For the purpose of the invention any plant, plant part, seed, pollen, ovule, embryo or somatic plant cell harboring nuclear genetic material derived from both *Allium ampeloprasum* and *Allium sativum* will be considered a hybrid plant or an interspecific hybrid plant.

It is easily within the reach of the skilled person to determine the presence of nuclear genetic material of both *Allium ampeloprasum* and *Allium sativum*. Such can be done for example by screening for the presence of genetic markers from both species. One way of performing such a screening method is by choosing sufficient genetic markers which are species-specific and cover the whole genome of each species in a sufficient manner and determining if at least one marker for each species is present in the plant. Of course the skilled person will be aware of other methods to assess whether nuclear genetic material of both *Allium ampeloprasum* and *Allium sativum* species is present in a plant.

The terms "nuclear genome" or "nuclear genomic material" are known to the skilled person and refer to hereditary traits which are present in the nucleus. Although such traits generally can be assumed to be encoded as genes by the nuclear DNA, it also includes hereditary traits such as non-coding DNA, epigenetic modifications present on the nuclear DNA and any other hereditary trait present in in the nucleus which may be passed along to daughter cells by cell division.

For the purpose of the invention the term "capable of producing seeds" should be interpreted as being capable of sexual reproduction, either by self-pollinating of cross pollinating, and therefore excludes plants that can reproduce solely or predominantly asexually through vegetative propagation. For the purpose of the invention "capable of producing seeds" should further be interpreted as capable of producing seeds on a scale allowing commercialization of such seed. Very occasional production of flowers allowing fertilization and development of very limited amounts of seed as for example is the case for garlic is therefore not within the scope of the invention. It would be clear to the skilled person that it is not possible to grow on a commercial scale garlic plants which are currently on the market with the aim of selling seed due to the very low incidence of seed development, while such commercial growing of seed would be possible with leek varieties currently on the market. Therefore an interspecific hybrid plant capable of producing seeds according to the invention therefore would allow the commercial growth of seeds for an interspecific hybrid plant according to the invention.

It should however be understood that plants according to the invention may also be propagated vegetatively. Therefore it is required that a plant according to the invention has at least functional female reproductive organs capable of producing seed. The presence of functional male reproduction organs is therefore not required for the invention and is entirely optional. The invention thus includes female (male sterile) plants. The term "capable of producing seeds" should further be interpreted to mean capable of producing seeds which can yield a new plant.

It has surprisingly be found that by creating such hybrid plant, the characteristic odor and taste properties derived from a garlic plant can be stably introduced in a leek-like hybrid plant.

The presence of organosulfur compounds is generally known to contribute to the specific odor and taste of garlic, in particularly the presence of alliin which is converted to allicin upon damage of the garlic plant through for example cutting or crushing. The so formed allicin is unstable and further degrades in other organosulfur compounds. Because allicin is directly or indirectly responsible for the typical garlic taste and odor, it is generally assumed that allicin levels in garlic are higher than in other plants, although allicin may still be present in (much) lower amounts, especially in related plants from the onion family. It is therefore an object of the invention to provide a hybrid plant with an increased amount of allicin. Preferably an increased amount of allicin is at least 250 mg/kg when determined in the white part of the leaf sheet of the plant. Preferably the increased amount of allicin present in the hybrid plant results in the plant having a garlic-like odor and or taste. Even more preferably, the plant has the appearance of leek and has an increased amount of allicin. More preferably, a hybrid plant resembling leek has one or to most two cloves.

For the purpose of the invention the amount of allicin can be determined according to the following method:

The white parts of the leaf sheet of the plants are isolated and freeze dried, the freeze dried parts are then analyzed. Part of the freeze dried powder of plants is weighed and re-suspended in water and incubated at room temperature to convert alliin to allicin. After alliin is converted to allicin, pH is raised to convert allicin to allyl disulfide. Allyl disulfide content is determined using gas chromatography and mass spectrometry (GC-MS). Based on the measured amount of allyl disulfide, total amount of allicin was calculated. The method is further described in the examples.

Therefore, in a preferred embodiment of the invention the interspecific hybrid plant contains at least 250 mg/kg of allicin when determined in the dried white part of the leaf sheet of the plant, preferably the white part of the leaf sheet of the plant is freeze dried.

Our experimental data demonstrate that allicin content in leek is around 100 mg/kg and in garlic around 5400 mg/kg as determined in the white part of the leaf sheet of the plant (see example 2). It is further shown that hybrid plants may have an allicin content similar to leek for hybrids scoring low in a smell test, or may have intermediate allicin content for hybrids scoring high in a smell test. Therefore, a hybrid plant according to the invention has at least 250 mg/kg of allicin as determined in the white part of the leaf sheet of the plant, preferably the allicin content is at least 300 mg/kg, more preferably at least 350 mg/kg, even more preferably at least 400 mg/kg even more preferably at least 500 mg/kg and most preferably 600 mg/kg as determined in the white part of the leaf sheet of the plant.

The skilled person is aware that freeze drying of samples in the above method may not be essential and samples may either be dried by different means or allicin can be determined in fresh plant material, and will further be aware that the observed allicin content may vary slightly depending on the method used for determining allicin.

In the context of the invention "obtainable from" should be interpreted as "derived from", or "obtained from". Therefore it is an embodiment of the invention to provide an interspecific hybrid plant derived from a cross between an *Allium ampeloprasum* plant and an *Allium sativum* plant, wherein said hybrid plant is capable of producing seed and contains nuclear genomic material derived from both said *Allium ampeloprasum* plant and said *Allium sativum* plant, wherein said interspecific hybrid plant contains at least 250 mg/kg of allicin when determined in the white part of the leaf sheet of the plant and further wherein said interspecific hybrid plant is derived from an interspecific hybrid plant as deposited under accession number NCIMB 42564.

Therefore, it is an further embodiment of the invention to provide an interspecific hybrid plant derived from a cross between an *Allium ampeloprasum* plant and an *Allium sativum* plant, wherein said hybrid plant is capable of producing seed and contains nuclear genomic material derived from both said *Allium ampeloprasum* plant and said *Allium sativum* plant, wherein said interspecific hybrid plant contains at least 250 mg/kg of allicin when determined in the white part of the leaf sheet of the plant and further wherein said interspecific hybrid plant is obtained from an interspecific hybrid plant as deposited under accession number NCIMB 42564.

In the context of the invention, the term "progeny" or "descendant(s)" refers to offspring both directly obtained as further generations which can be derived from a plant of the invention. It also refers to directly obtained and further generations of offspring which are derivable or obtainable from a plant of the invention. Progeny may be derived from natural processes, such as self- or cross fertilization and subsequent growing of seeds, but progeny may also be derived from cell culture, tissue culture, regeneration or other means. The term interspecific hybrid in view of the invention should be understood as a plant which is either the direct result or from a cross between two different plant species or progeny of a plant which is the direct result of a cross between two plant species, and wherein said hybrid plant has genetic elements of both species in its nuclear genome. An interspecific hybrid according to the invention is the result of a cross between an *Allium ampeloprasum* plant with an *Allium sativum* plant and results in a plant harboring genetic elements of both species in its nuclear genome. Such crossing may be achieved by fertilization of the ovules of an *Allium ampeloprasum* plant by pollen of an *Allium sativum* plant, or by fertilization of the ovules of an *Allium sativum* plant by pollen of an *Allium ampeloprasum* plant. It should however be understood that "cross" is not limited to naturally occurring fertilization methods and can also be achieved by other methods known to the skilled person. For the purpose of the invention a cross between an *Allium ampeloprasum* plant and an *Allium sativum* plant should therefore be considered any process resulting in a plant, seed, part of a plant, embryo or somatic cell containing nuclear genomic material of both *Allium ampeloprasum* and *Allium sativum*.

In the context of the invention an F1 hybrid is the first generation offspring of distinctly different parent plants. In the context of the invention the parents are usually but not necessarily substantially homozygous plants. It is generally known that the use of F1 hybrids is desirable to produce plants with predictable genetic traits but lacking inbreeding depression, therefore resulting in stronger more vigorous plants.

In the context of the invention, vegetative propagation is the propagation of a plant by growing it from any structure entirely consisting of somatic cells. For the purpose of the invention, garlic is typically vegetatively propagated through the cloves, but may also be vegetatively propagated from the bulbils. Vegetative propagation in its natural form should be seen as any way the plant can propagate, i.e. create new plants, not involving the seeds, as propagation through the seeds relies on embryonic (non-somatic) cells.

In the context of the invention a leek-like plant should be interpreted as an interspecific hybrid plant resulting from a cross between an *Allium sativum* and an *Allium ampeloprasum* plant, which has the morphological characteristics of a leek plant, such as a long cylinder of leaf sheets and a scape producing an umbel of flowers.

In a preferred embodiment of the invention the interspecific hybrid plant is heterozygous for at least 35 markers selected from the group consisting of SEQ ID No. 1 to SEQ ID No. 65, preferably at least 40 markers, more preferably at least 45 markers, even more preferably at least 50 markers, even more preferably at least 55 markers, most preferably at least 60 markers.

In a most preferred embodiment of the invention the interspecific hybrid plant is heterozygous for each of the markers represented by SEQ ID No. 1 to SEQ ID No. 65.

In the context of the invention, a plant is heterozygous for a marker if in that plant both the allele corresponding leek and the allele corresponding to garlic can be detected. For example the sequence of SEQ ID No: 1 is TGAAAC-CAAATAGTATTCTTGGACTCTCCCATGGATTCCTTT-TAGGCCACCTGCAGTC GCTTGGCCTTGATTTTCC-TAAGAACATCAGTGTAGTTGCTGT[A/G]TGCCCCA-AGGGC ATGGGCCCATCAGTAAGAAGGCTCTATGT-CCAAGGAAAGGAAGTCAATGGTGCTGG CATTAAT-GCTAGCTTTGCTGTTCACCAGGATG; the SNP has been indicated in table 5 where the "G" allele corresponds to leek and the "A" corresponds to garlic. Therefore, a plant is heterozygous for the marker with SEQ ID No: 1 if both the leek and the garlic allele can be detected, meaning both the sequences:
TGAAACCAAATAGTATTCTTGGACTCTCCCATGGAT-TCCTTTTAGGCCACCTGCAGTC GCTTGGCCTTGAT-TTTCCTAAGAACATCAGTGTAGTTGCTGT[G]TGCC-CAAGGGCA TGGGCCCATCAGTAAGAAGGCTC-TATGTCCAAGGAAAGGAAGTCAATGGTGCTGGC A-TTAATGCTAGCTTTGCTGTTCACCAGGATG (SEQ ID NO: 66); and
TGAAACCAAATAGTATTCTTGGACTCTCCCATGGAT-TCCTTTTAGGCCACCTGCAGTC GCTTGGCCTTGAT-TTTCCTAAGAACATCAGTGTAGTTGCTGT [A]TGCC-CAAGGGCA TGGGCCCATCAGTAAGAAGGCTC-TATGTCCAAGGAAAGGAAGTCAATGGTGCTGGC ATTAATGCTAGCTTTGCTGTTCACCAGGATG (SEQ ID NO: 67),
can be detected in the plant resulting in a heterozygous score for the SNP. Table 5 indicates the location of each SNP within the SEQ ID No. corresponding to each marker used herein. Table 5 also indicates which allele of the sequence corresponds to garlic and which allele corresponds to leek.

Interspecific garlic-leek SNP markers were identified from cDNA sequences and tested on garlic and leek plants. 179 of these markers gave good product and information between all tested garlic and leek plants. Of these markers, 151 could be assigned to 16 linkage groups. Of these 151 markers eventually 65 were selected covering all linkage groups and used as a selection tool. These markers are listed in table 5 and indicated with their respective SEQ ID No, sequence and polymorphism.

Using these markers a plant can be scored for each locus to have a leek genotype, a garlic genotype or to have a heterozygous genotype. For the purpose of using these markers, a locus identified as leek-like means no corresponding garlic polymorphism was identified, a locus identified as garlic-like means no corresponding leek polymorphism was identified, and a locus identified as heterozygous both the polymorphism corresponding to garlic and the polymorphism corresponding leek can be identified. The markers are listed in table 5

Therefore a plant according to the invention being heterozygous for a certain marker should be interpreted as a plant wherein both the polymorphism corresponding to leek and the polymorphism corresponding to garlic for that specific marker can be detected. The garlic and leek specific polymorphisms corresponding to a genetic marker are indicated in table 5.

A single nucleotide polymorphism (SNP) in the context of the invention is stretch of DNA which is identical between leek and garlic with the exception of a single nucleotide, which differs between garlic and leek and can therefore serve as an identifier for retracing the origin of the stretch of DNA. Polymorphism in the context of the invention refers to single nucleotide polymorphism (SNP) being a naturally occurring or genetically introduced variation of a single nucleotide.

In a preferred embodiment of the invention further at least one, preferably at least two, most preferably three of the odor compounds selected from the group consisting of methyl allyl disulfide, propenyl methyl disulfide and diallyl disulfide is present in the white part of the leaf sheet of the plant.

The allicin produced by conversion of alliin by alliinase is not stable and forms several other organosulfur compounds, such as diallyl disulfide, diallyl trisulfide, propenyl methyl disulfide, vinyldithiins, ajoene and allyl methyl sulfide. Generally the presence of these compounds including allicin contributes to the specific odor and taste from garlic. Although all these compounds may be formed through degradation of allicin, these compounds may also be naturally occurring in a plant or be derived from a different source. Therefore it was an object to identify compounds that are present in garlic plants but absent or present in relatively low amounts in leek plants. Preferably such compounds are garlic specific. Therefore it is an object of the invention that one or more garlic compounds are present in the hybrid plant.

It was found in an initial test that four peaks could be detected in a GC-MS sniff experiment which are present exclusively in garlic and not in leek. These peaks correspond to the compounds methyl allyl disulfide, propenyl methyl disulfide, diallyl disulfide and an unknown compound. In a further experiment, leek and garlic reference samples as well as hybrid plants were tested for the presence of 2,5-dimethylthiophene, methyl allyl disulfide (methyl 2-propenyl disulfide), diallyl disulfide (di-2-propenyl disulfide) and propenyl methyl disulfide (methyl 1-propenyl disulfide). It was found that 2,5-dimethylthiophene can be detected in leek in comparable amounts to garlic and therefore, the presence of 2,5-dimethylthiophene may not be indicative of a odor or taste specific for garlic, although it may contribute to the overall odor and taste of garlic.

For the purpose of the invention "methyl allyl disulfide, propenyl methyl disulfide or diallyl disulfide is present" should therefore be interpreted as the presence of these compounds can be demonstrated using the GS-MS sniff experiment as outlined in example 2. A compound can be detected when a peak and corresponding retention time can be observed which correspond to said compound, and identified as being said compound by further MS analysis. Ideally, pure compounds and garlic and leek extracts are included in the experiments as positive and negative controls. Preferably a substance can be detected if the peak area of the sample to be tested has at least 1% of the surface area of a garlic sample after correction for total sample amount.

It is known to the skilled person that compounds may also be known under different names but refer to the same structural formula and thus the exact same compound. Therefore with reference to the invention, methyl allyl disulfide is also known as methyl 2-propenyl disulfide and refers to the compound with the structural formula on line 7 of the table in FIG. 1. Therefore with reference to the invention, propenyl methyl disulfide refers to the compound with the structural formula on line 6 of the table in FIG. 1. Therefore with reference to the invention, diallyl disulfide is also known as di-2-propenyl disulfide and refers to the compound with the structural formula on line 4 of the table in FIG. 1.

In a further preferred embodiment of the invention
the amount of methyl allyl disulfide is at least 25 mg/kg as determined in the white part of the leaf sheet of the plant, and/or
the amount of diallyl disulfide is at least 50 mg/kg as determined in the white part of the leaf sheet of the plant.

It was found that methyl allyl disulfide, propenyl methyl disulfide and diallyl disulfide can be detected in garlic plants but can essentially not be detected in leek plants, and moreover that the presence of these compounds can be detected in preferred hybrid plants of the invention. In subsequent experimentation the presence of methyl allyl disulfide and diallyl disulfide was quantified in a garlic plant, a leek plant and a number of hybrid plants. Due to the inability to find a suitable source of pure propenyl methyl disulfide (methyl 1-propenyl disulfide), no quantification was done for this compound. It was demonstrated that presence of these compounds correlates to the presence or absence of garlic odor in hybrid plants. The amount of methyl allyl disulfide in the garlic reference plant was 550 mg/kg and in hybrid plants ranged from 0 to 260 mg/kg, with plants with a more garlic-like odor generally having higher amounts methyl allyl content. The amount of diallyl disulfide in garlic was determined to be 2300 mg/kg, with the amount in hybrid plants ranging from 0 to 430 mg/kg, again a correlation with amount of the compound quantified and garlic like odor was found.

Therefore in a more preferred embodiment of the invention
the amount of methyl allyl disulfide is at least 25 mg/kg, preferably 50 mg/kg, more preferably 100 mg/kg most preferably 150 mg/kg as determined in the white part of the leaf sheet of the plant, and/or
the amount of diallyl disulfide is at least 50 mg/kg, preferably 100 mg/kg, more preferably 150 mg/kg most preferably 200 mg/kg as determined in the white part of the leaf sheet of the plant.

For the purpose of the invention methyl allyl disulfide, propenyl methyl disulfide and diallyl disulfide can be detected and/or quantified using GS-MS methods known to the skilled person, by analyzing the corresponding surface under the peak area from a fraction obtained from fresh white part of the leaf sheet of a plant and comparing this with a control peak obtained from a known amount of source reference material. The reference material will usually be a pure source of methyl allyl disulfide, propenyl methyl disulfide and/or diallyl disulfide.

In a further preferred embodiment of the invention the interspecific hybrid plant has a garlic odor and/or taste. Preferably said odor can be detected with a garlic smell test In a further embodiment of the invention the interspecific hybrid plant is male sterile. Preferably said hybrid plant is cytoplasmic male sterile.

A sterile plant is known to the skilled person to be a plant with either defective male or defective female reproduction organs, resulting in a fully female or male plant respectively, although it is noted that fully sterile (both male and female sterile) plants are also known. Fully male or fully female plants are not able to self-pollinate but may still reproduce by crossing with another plant (but the latter not in the case of fully sterile plants). Male sterility is caused by absence of pollen or the inability of pollen to fertilize a female plant. The underlying cause may be genetically encoded by nuclear DNA, resulting in Genic Male Sterility (GMS) or may be encoded by mitochondrial DNA resulting in Cytoplasmic Male Sterility (CMS).

In a further embodiment of the invention the interspecific hybrid plant is derived from cytoplasmic male sterile *Allium sativum* or derived from cytoplasmic male sterile *Allium ampeloprasum*.

The skilled person will appreciate that the invention as laid down above is not limited to the first aspect of the invention and the subsequently described preferred embodiments, but that also combinations of preferred embodiments may be made. The invention as presently claimed therefore extends to the hybrid plant according to the first aspect of the invention with any combination of preferred embodiments as described above.

It is a further aspect of the invention that the invention also encompasses plant parts, seeds, edible parts, pollen, egg cells, protoplasts, callus, cultured cells, cultured tissues, somatic embryos or zygotic embryos of an interspecific hybrid plant according to the invention.

In a second aspect of the invention is provided a method (henceforward referred to as "the method") of generating an interspecific hybrid plant, the method comprises the steps of:

1) crossing an *Allium ampeloprasum* plant with an *Allium sativum* plant;
2) screening progeny with the markers identified with SEQ ID Nos: 1 to 65;
3) selecting progeny which are heterozygous for at least 35 markers selected from the group consisting of SEQ ID Nos: 1 to 65; and optionally:
4) crossing the progeny selected in step (3) with *Allium ampeloprasum* or *Allium sativum*.

In one embodiment of the invention step (2) is performed with markers identified with SEQ ID Nos 1 to 65 as listed in table 5, and in step (3) etc. progeny is selected which can be scored heterozygous for at least 35 of the markers tested in step (2). In a preferred embodiment of the invention, in step (3) progeny is selected that score heterozygous for at least 40 of the markers tested in step (2), more preferably score heterozygous for at least 45 of the markers tested in step (2), even more preferably score heterozygous for at least 50 of the markers tested in step (2), even more preferably score heterozygous for at least 55 of the markers tested in step (2), most preferably score heterozygous for at least 60 of the markers tested in step (2). In another most preferred embodiment, in step (3) progeny is selected which score heterozygous for all markers tested in step (2).

In a preferred embodiment of the invention in step (2) of the method further comprises determining the allicin content of the progeny in the white part of the leaf sheet of the plant and step (3) further comprises selecting progeny having an allicin content of at least 250 mg/kg in the white part of the leaf sheet of the plant.

In a preferred embodiment of the invention in step (3) progeny is selected with an allicin content of at least 300 mg/kg, in a more preferred embodiment at least 350 mg/kg allicin, even more preferred at least 400 mg/kg allicin, even more preferred at least 450 mg/kg allicin, in a most preferred embodiment at least 500 mg/kg allicin. The skilled person is aware that the different preferred embodiments for number of heterozygous scored markers and allicin levels may be combined as desired in order to make the selection more or less strict.

In a further preferred embodiment of the invention step (2) of the method further comprises determining the content of methyl allyl disulfide and diallyl disulfide in the white part of the leaf sheet of the plants, and step (3) further comprises selecting plants having an methyl allyl disulfide content of at least 25 mg/kg and/or having a diallyl disulfide content of at least 50 mg/kg.

The marker based selection of progeny may be supplemented with selection based on plant content analysis, more specifically by analyzing the levels of allicin and/or analyzing the levels of methyl allyl disulfide and/or analyzing the levels of diallyl disulfide.

In an embodiment of the invention in step (3) plants are selected having a methyl allyl disulfide content of at least 25 mg/kg and/or having a diallyl disulfide content of at least 50 mg/kg. Preferably, in step (3) plants are selected having a methyl allyl disulfide content of at least 30 mg/kg, more preferable at least 35 mg/kg even more preferably 40 mg/kg or most preferably at least 45 mg/kg. Preferably in step (3) plants are selected having a diallyl disulfide content of at least 55 mg/kg, more preferably at least 60 mg/kg, more preferably at least 65 mg/kg, even more preferably 70 mg/kg or most preferably 75 mg/kg. The skilled person is aware that the different preferred embodiments for the number of heterozygous scored markers, allicin levels, methyl allyl disulfide levels and diallyl disulfide levels may be combined as desired in order to make the selection more or less strict.

In a further preferred embodiment of the invention the *Allium sativum* plant and/or the *Allium ampeloprasum* plant in step (2) of the method is cytoplasmic male sterile.

In a third aspect of the invention is provided an use of an interspecific hybrid plant according to the invention, or plant parts, seeds, edible parts, pollen, egg cells, protoplasts, callus, cultured cells, cultured tissues, somatic embryos or zygotic embryos of an interspecific hybrid plant according to the invention, or a method according to the invention, to obtain seeds capable of growing an interspecific hybrid plant derived from a cross between an *Allium ampeloprasum* plant and an *Allium sativum* plant.

FIGURES

FIG. 1 shows an overview of the chemical formulas and names of alliin and organosulfur compound derived from alliin. For some compound commonly used alternative names are given between brackets.

EXAMPLES

Example 1: Generation of a Cross Between *Allium sativum* and *Allium ampeloprasum* and Selection Based on Odor Interspecific crosses were performed between a cytoplasmic male sterile garlic plant and leek. F1 plants from these crosses show strong heterosis, and often have a strong garlic odor.

F1 hybrid plants were first scored based on phenotype and characterized as bulb type, fine type or intermediate type. As a preliminary assessment of useful hybrid plants in the breeding program, a smell test was deployed. For this, all individual plants were scored by four separate testers based on odor, giving a score ranging from 0-9 where 0 corresponds to the odor of leek and 9 corresponds to the odor of garlic. Plants were selected for the breeding program based on useful characteristics and a high score in the smell test.

Example 2: Determining Garlic Specific Compounds in Hybrid Plants

In order to determine whether the smell test scores obtained correlate with the presence of garlic specific compound a series of experiments were designed. First the amount of allicin was determined in a leek plant, a garlic plant and two hybrid plants, one having a high score (garlic like odor) and one having a low score (leek like odor) as determined in the smell test. For this, the white part of the leaf sheet of the plants was freeze dried and sent for analysis. Part of the freeze dried powder of plants is weighed and re-suspended in water and incubated at room temperature to convert alliin to allicin. After alliin is converted to allicin, pH is raised to convert allicin to allyldisulfide. Allyldisulfide content is determined using gas chromatography and mass spectrometry (GC-MS). Based on the measured amount of allyldisulfide, total amount of allicin was calculated. Results are listed below in table 1. The results demonstrate, as expected, a much higher allicin content in garlic plants as compared to leek. Allicin content of the hybrid shows correlation with the smell test scores, with the low scoring plant having similar allicin content as leek and the high scoring plant having much higher allicin content, albeit not as high as garlic.

TABLE 1

Allicin content of a leek plant, a garlic plant, and two hybrid plants.

| Plant | Allicin (mg/kg) | Score smell test (0-9) |
|---|---|---|
| Leek | 110 | 0 |
| Garlic | 5400 | 9 |
| Fz1-21 | 650 | 8 |
| Fz1-28 | 90 | 1 |

Allicin content was determined as amount of allicin per unit of weight of the freeze dried plant by measuring allyldisulfide content by GC-MS and calculating the corresponding amount of allicin. Amounts were shown together with the scores obtained from the smell test for these plants.

As the amount of allicin is determined indirectly and only accounts for garlic odor and taste upon its further conversion, the same plants as described above were subjected to GC-MS-sniff analysis to see whether garlic specific compounds can be detected.

For further analysis of garlic specific compounds, a GC-sniff experiment was combined with a GC-MS experiment to detect and quantify volatile substances which may be garlic specific. Several hybrid plants were sampled, together with leek and garlic controls. For these experiments, white parts of fresh plants were taken and extracts were obtained using the Likens-Nickerson distillation-extraction method. The thus obtained extracts were analyzed on volatile compound profile using gas chromatography in combination with sniff technology (GC-sniff) and gas chromatography combined with mass spectrometry (GC-MS).

Results are displayed below in table 2. The four compounds shown could not be detected in leek, but could be detected in garlic. The hybrid plants show presence of at least three garlic specific compounds.

TABLE 2

Presence of garlic specific compounds in a leek plant, a garlic plant, and two hybrid plants as determined by GC-MS-sniff analysis.

| Plant | methyl allyl disulfide | propenyl methyl disulfide | diallyl disulfide | unknown |
|---|---|---|---|---|
| Leek | not. det. | not. det. | not. det. | not. det. |
| Garlic | 279 | 21.5 | 743 | 173.4 |
| Fz1-21 | 38 | 23.1 | 40.1 | 72.6 |
| Fz1-28 | 4.4 | not. det. | 9.7 | 25.4 |

Indicated values are total surface area under peak.

To further expand on these results a more elaborate experiment was performed using a greater number of hybrid plants. In this experiment presence of the following substances was determined: dimethylthiophene, methyl allyl disulfide (methyl 2-propyl disulfide), diallyl disulfide (di-2-propenyl disulfide) methyl 1-propenyl disulfide. These results are displayed in Table 3. The results demonstrate that the amount of dimethylthiophene is comparable in garlic and leek and therefore not a suitable indicator for garlic odor or taste. Amounts of methyl allyl disulfide, diallyl disulfide and methyl 1-propyl disulfide were high in garlic and nearly absent in leek. Hybrid plants show either absence or a varying degree of presence of the compounds, where presence or absence of methyl allyl disulfide, diallyl disulfide and methyl 1-propyl disulfide demonstrated a correlation with the results obtained with the garlic smell test.

TABLE 3

Peak area for specific compound for each freeze dried plant sample, normalized to garlic.

| Sample | 1 | 2 | 2,5-dimethylthiophene | methyl allyl disulfide | diallyl disulfide | propenyl methyl disulfide |
|---|---|---|---|---|---|---|
| 2455 | − | − | 17 | 0.2 | 0 | 25 |
| 2456 | − | ± | nd | nd | nd | nd |
| 2457 | ± | ± | 120 | 0.3 | 0 | 160 |
| 2458 | ± | ± | 26 | 4 | 1 | 35 |
| 2459 | ± | ± | 21 | 3 | 1 | 26 |
| 2460 | ± | ± | 24 | 6 | 1 | 67 |
| 2461 | ± | ± | 24 | 9 | 4 | 56 |
| 2462 | ± | − | 15 | 8 | 3 | 42 |
| 2463 | ± | ± | 69 | 0 | 0 | 19 |
| 2464 | − | − | 39 | 0 | 0 | 19 |
| 2465 | ± | ± | 22 | 4 | 2 | 22 |

TABLE 3-continued

Peak area for specific compound for each freeze dried plant sample, normalized to garlic.

| Sample | 1 | 2 | 2,5-dimethylthiophene | methyl allyl disulfide | diallyl disulfide | propenyl methyl disulfide |
|---|---|---|---|---|---|---|
| 2466 | ± | − | 12 | 2 | 0.6 | 16 |
| 2467 | − | − | 14 | 4 | 2 | 33 |
| 2468 | − | − | 44 | 3 | 0.8 | 48 |
| 2469 | ± | − | 21 | 2 | 0.6 | 21 |
| 2470 | ± | ± | 18 | 28 | 14 | 79 |
| 2471 | ± | + | 61 | 16 | 11 | 90 |
| 2472 | ± | − | 8 | 27 | 11 | 53 |
| 2473 | ± | ± | 19 | 22 | 11 | 72 |
| 2474 | ± | + | 35 | 45 | 18 | 140 |
| 2475 | ± | + | 12 | 39 | 20 | 50 |
| 2476 | ± | ± | 7 | 23 | 17 | 31 |
| 2477 | ± | + | 9 | 27 | 14 | 52 |
| 2478 | ± | + | 13 | 44 | 13 | 100 |
| 2479 | ± | + | 8 | 21 | 18 | 29 |
| garlic reference | nd | nd | 100 | 100 | 100 | 100 |
| leek reference | nd | nd | 74 | 0.1 | 0 | 0 |

First column indicates the sample ID, second and third column give an independent smell test ("−" leek like; "+/−" some garlic odor; "+" strong garlic odor), next columns give relative (garlic = 100%) peak areas for each indicated compound, "nd" is not determined; sample 2456 was lost.

In order to quantify these results the peak areas obtained were compared with known amounts of reference substances. No reference sample of methyl 1-propenyl disulfide could be obtained so these data are omitted. Calculated amounts are shown in table 4 in mg/kg freeze dried plant weight.

TABLE 4

Quantification of three compounds in different samples.

| Sample | 1 | 2 | 2,5-dimethylthiophene | methyl 2-propenyl disulfide | di-2-propenyl disulfide |
|---|---|---|---|---|---|
| 2455 | − | − | 4 | 1 | 0 |
| 2457 | ± | ± | 28 | 2 | 0 |
| 2458 | ± | ± | 6 | 23 | 27 |
| 2459 | ± | ± | 5 | 17 | 33 |
| 2460 | ± | ± | 5 | 36 | 35 |
| 2461 | ± | ± | 6 | 58 | 98 |
| 2462 | ± | − | 3 | 52 | 78 |
| 2463 | ± | ± | 15 | 0 | 0 |
| 2464 | − | − | 8 | 0 | 0 |
| 2465 | ± | ± | 5 | 25 | 47 |
| 2466 | ± | − | 3 | 9.5 | 14 |
| 2467 | − | − | 3 | 25 | 40 |
| 2468 | − | − | 10 | 17 | 19 |
| 2469 | ± | − | 5 | 9.6 | 16 |
| 2470 | ± | ± | 4 | 170 | 340 |
| 2471 | ± | + | 13 | 98 | 270 |
| 2472 | ± | − | 2 | 170 | 260 |
| 2473 | ± | ± | 4 | 140 | 270 |
| 2474 | ± | + | 7 | 260 | 420 |
| 2475 | ± | + | 2 | 210 | 430 |
| 2476 | ± | ± | 1 | 130 | 390 |
| 2477 | ± | + | 2 | 150 | 310 |
| 2478 | ± | + | 2 | 230 | 290 |
| 2479 | ± | + | 2 | 110 | 400 |
| garlic reference | nd | nd | 20 | 550 | 2.300 |
| leek reference | nd | nd | 14 | 0.4 | 0 |

First column indicates the sample ID, second and third column give an independent smell test ("−" leek like; "+/−" some garlic odor; "+" strong garlic odor), next columns give approximation of compound content by comparing the peak area with a known standard and dividing by the sample weight.

Example 3: Marker Assisted Selection

Using genome painting of BC1 hybrid plants so far no crossing over of garlic and leek chromosomes has been observed. Therefore it is assumed that in the backcross program, garlic chromosomes may be lost. It is therefore important to determine which garlic chromosome(s) need to be maintained for the garlic odor, and if a stable configuration of garlic/leek chromosomes can be identified. From the literature a limited genetic map (with only 30 markers on 9 linkage groups) of garlic is available.

Garlic-leek interspecific SNPs have been identified based on cDNA sequences of leek and garlic. From the available sequence data many thousands of SNP-assays can be designed. Based on quality scores of the sequence depth and occurrence of other sequence polymorphisms near the SNP, 288 SNP-assays have been developed and tested on 16 garlic lines and 9 leek lines. 179 of those markers gave products and are informative between all tested leek and garlic lines. Secondly, the presence of garlic DNA in 21 lines of leek back-crossed interspecific garlic-leeks was tested. It was expected that all markers would group together in 8 chromosomal groups thereby showing the presence or absence of a specific garlic chromosome. Surprisingly, it was found that 151 markers grouped into 16 linkage groups and 28 markers could not be grouped to any of the other markers.

Using these markers a plant can be scored as "leek", "garlic" or heterozygous for that specific marker, depending on the detected allele. Based on the marker data it was not possible to determine how many copies of genomic material are present and whether the garlic alleles are present in addition to the leek chromosomes or are integrated in the genomic material by crossing over.

Leaf samples for DNA isolation have been taken from plants that have been phenotypically characterized on odor. With the newly developed leek-garlic interspecific markers it was possible to asses for each plant the presence or absence of (a part of) the 16 linkage groups. Unfortunately, no single linkage group of garlic (or marker) could be identified as essential for strong garlic odor. However, a positive correlation was observed between the intensity of garlic odor and the presence of more garlic linkage groups.

From the available useful markers about 50 markers were selected covering all 16 linkage groups (table 5), these markers provide a useful set for selection of interspecific hybrid plants with garlic taste and/or odor. It was observed that the presence or absence of garlic specific compounds could not be attributed to a single linkage group. Plants heterozygous for all 50 markers were selected for further propagation.

TABLE 5

Markers used for selection of interspecific hybrid plants. Indicated are the SEQ ID No., the alleles corresponding with leek or garlic respectively, the linkage group they are mapped to and the sequence including the polymorphism for leek and garlic. Naturally occurring polymorphisms not linked to either the leek or garlic genotype are indicated using IUPAC nucleotide code, where R = A or G; Y = C or T; S = G or C; W = A or T; K = G or T; and M = A or C.

| SEQ ID No. | Leek | Garlic | Linkage group | Sequence |
|---|---|---|---|---|
| 1 | G:G | A:A | A.1 | TGAAACCAAATAGTATTCTTGGACTCTCCCATGGA TTCCTTTTAGGCCACCTGCAGTCGCTTGGCCTTGAT TTTCCTAAGAACATCAGTGTAGTTGCTGT[A/G]TGC CCCAAGGGCATGGGCCCATCAGTAAGAAGGCTCT ATGTCCAAGGAAAGGAAGTCAATGGTGCTGGCATT AATGCTAGCTTTGCTGTTCACCAGGATG |
| 2 | C:C | T:T | A.1 | CCTGCTCCCTCTGTGCCTGCATATCCCGTTCATTCT TTTCGGCAAGTGCTTTGGCCGCCCTCTCTGATGTTC TTTGGTGCCTTTCGAGTCTAGCTCTTCT[T/C]CGTTC TTCGGTTTCTCCTTCAACTTCTTGAAAGTTCCCAGA TGATGAGCCACCTCCAAAAATAGAGGTCAGGTCAT CAACAATATTTGTTGTGGAAGATG |
| 3 | T:T | G:G | A.1 | AAGAGAAAACGGGCTCCTTAACAAGACCTTGTTCG ACCATACTGTACCAGACTGGCTTTGCCTTGCCAAC TGAGATCTCCTGAAATCCAAGCCCAAGAAT[G/T]CC ATCAAACTTGGCTACCAGGAAAGTCAGACCAGGCT CTCTGGTGGCTTCAATAAATTCCTGATTTTTCACAA CAAGGTCCCCTAATTTGACAGAATCTT |
| 4 | T:T | C:C | A.1 | TTTTACCACGGTATTCCTTGATCATAACCACATGAT TTTCATTCCCTCTGCTCTCTTCTTTCTGCTCAATAGA AGATATGATTCTCCAAGAAGCACGGCG[C/T]GCCC CAATAACATTTTTGTATGCAACTGAAAGGAGGTTC CTCTCTTCTACAGTAAGTTCTTCAGCATCAACTGAT TTTGCTACCTTTTCCATGAACTCAA |
| 5 | T:T | C:C | A.2 | ACCCRCTMMTCGGATTCTGGCGCCACATTGGCACC TCCCAGTCCTTGRTCTTCTTCGAATGGGCCCTGAC YGCATCACYGGRTCCCGCATTGTCCCGAC[C/T]AAA GAGGCKRACAGTTATGGAGTTGTTAAAGTTCCTTT CTTGTGGCTAGSGATATCAAAGGAAGGAGAGGCG GTGAGTTATTGGTTGGAGGAAGAGGATC |

TABLE 5-continued

Markers used for selection of interspecific hybrid plants.
Indicated are the SEQ ID No., the alleles
corresponding with leek or garlic respectively, the
linkage group they are mapped to and the sequence including
the polymorphism for leek and garlic. Naturally
occurring polymorphisms not linked to either the leek or
garlic genotype are indicated using IUPAC nucleotide code,
where R = A or G; Y = C or T; S = G or C; W = A or T;
K = G or T; and M = A or C.

| SEQ ID No. | Leek | Garlic | Linkage group | Sequence |
|---|---|---|---|---|
| 6 | A:A | G:G | A.2 | CAAGCACGAAAACAAGCTCCTTCTCATCCGGAAAC TTCAGTCTCATTATCTCAAATGGATCGTAGCTTCTT ACCAGAACGAAACCACCAAGAATAGCAGG[G/A]G CGATGTTATCTGCATGGTAACCACTAACCCTCTTCT CTGATTCCAATCCTGCGAGGATAAGGTCATCATCA TCCAAAATATTTCCAAAGAAAGCATTGA |
| 7 | A:A | G:G | G.1 | AAGCCATYRAGAAAATCTTRAYYSRTAACAGTAAA GGAATYAACTRTCARATYYWRTCRAATCYAGAAT TTCWMGCAGAAGGCACTRCAATTGAAGATTT[G/A] TTCAARCCAGATCRTGTACTGAYYGGYGGACGTGA AACKCYCGAMRGGCARAAGGCRKTTMRAGCRCTT AAAGCGGTGTATGCTAATTGGGTGCCTGAA |
| 8 | G:G | A:A | G.2 | TGCTGGTTGGGCAGATAAGATACATGGGCTTATAG TCCCGGCCGATGGGCCCCATCACGTTCAGGTTCTG TACGAACCAATTGGTGTTGCAGGGCAAATC[A/G]TT CCTTGGAATTTCCCTCTTCTTATGTTTGCTTGGAAA GTTGGTCCAGCTTTAGCAACTGGAAACGTTGTTGT ACTTAAGACTGCAGAACAGACCCCTTT |
| 9 | A:A | G:G | G.2 | ACCTGGCTAAGTGCGCAGTGGAAAACAAGCGTGT CTTTTCCCTTCACCGCCTGCAAAAGCTGAGGCATC TTCTCATGAAACGATTCGCTAGCGTAGTGAT[G/A]A GATCCTGCTATATGCGCATCATAACTCCTCTCGTCG TCTCTGACGTCGATTATGGCGACTCTCGCAGTTCTA TTGAGTAAGATTAGTTGGGATGGGGAA |
| 10 | T:T | C:C | G.2 | ATTACACAGATATGAGTAAATTGTATGAGAAGTAC AAGGATCAAGGATTGGAGATCCTTGCTTTTCCTTG CAACCAGTTTAACTCACAAGAGCCAGGAAC[C/T]G ATGAGGAGATTGTGAATTTTGTTTGCACACGCTTC AAGGCTGAATATCCCATCTTTAGCAAG |
| 11 | C:C | T:T | G.2 | TTGCTCGATCAACAAGAAGAATGGTCAGAAACAC CACATAGAAATAAGGTAGAAAATGATCAAAAAGT GCCGGCACACTCCAACAGAATGCAGCAGATAT[T/C] TCTGGTGCGTAGTGGAAGTGGCGTGCAAGACCCC ACCATCCAGAGGTCAAAAGAAGACTGGTTTTTGTT TCCCCTTTTGTGGTCGTATAAGAGGCAACTA |
| 12 | A:A | G:G | G.2 | GACCAGCTGCAGACATGAATCCTAGAGCCTCGTCT ACTCTATGCGCTAACTCCAGGTACCTATCCCCTTGC TCGCTGTGCTGTGTAAAATCAAGATTCCA[G/A]TGA GTAACCCGCTGCATGGCAGCATAACCTCCAGTGGC AAATGCCCTCAAAAGATTAAGAGTAGCAGCAGCC TGACAGTATGCACGAACCATTCTATGCG |
| 13 | T:T | C:C | B.1 | CAATTAGTGGCCCGAAACGTTTAATGAAAGATCTA TATGCCGGCAATAAAACTTCAGCAACAGCAAGCCT CAAAGACTCACGTAACTCTGGGTCAGGTAC[C/T]GC CCACTGAGATTGCCTTTGATGAAGCTCCTCAAATT GCATGTTGAATGTCTTGAGCCTCTCTTTTATGGCAG CTCTAGAAACACCGCTGCTGTTTCCAC |
| 14 | G:G | C:C | B.1 | TGACGGAGGCAAACCTCATGTTATCAGAGGACAA AGACCTTTTTGCAGGAAAAAGGAGACTATCCAAAT TGAGGCGCAGAGCATGAAATATCATAGGGAA[C/G] ACCAACATAAGATGAAGGGCGTAGCTCACTCGAA CAATGTCGCTAAAAATATGTGAACATGGGATTCCA AGATCGGTGTCAAAGTTTGCAAGGACATCAT |

TABLE 5-continued

Markers used for selection of interspecific hybrid plants. Indicated are the SEQ ID No., the alleles corresponding with leek or garlic respectively, the linkage group they are mapped to and the sequence including the polymorphism for leek and garlic. Naturally occurring polymorphisms not linked to either the leek or garlic genotype are indicated using IUPAC nucleotide code, where R = A or G; Y = C or T; S = G or C; W = A or T; K = G or T; and M = A or C.

| SEQ ID No. | Leek | Garlic | Linkage group | Sequence |
|---|---|---|---|---|
| 15 | C:C | T:T | B.1 | CTCGGTAGTCATACTCGTCGAAGTACGCTCTTCTCT GCTCTTTCGACAGCTTCTGTAGCTGCGATTTTTTCA ATGGCTTGAAAGGTGGGAGAGAATCATA[T/C]TCA TCTTCTTCTTCAAAATCATCAAAATCGAACTCATCG AGATCAATATCGGAGTCGACGCCATTATCGCCTTG TTC |
| 16 | C:C | T:T | B.1 | TTCTTCAAATACCCTCAAAATAATTGATCTGAGCT AACAGATGACAGGAGATCGACGAATTGGAGTAGC GGTGGACTTCTCCTCATGCAGCAAAGCGGCG[T/C]T GAGGTGGGCGATCGAAAATCTGGCGCGTGATGGA GACCATCTGATTTTAATCAACGTTCAAAAGAAGG GTTTTATGAAACTGGCGAGATGCAACTATG |
| 17 | T:T | C:C | B.2 | ATCTGGGGATCTCTGGCCTTACATTCTGACGAACA ACAGCAGAAGTGAGTTCGGCAAAAGAAAGATTAG GATATGGCATATCACAACAATAAATCTCCCA[C/T]A GGCAAATTCCAAAGCTGTATACATCACATCTTCTA TTGTATGGTTTTCCTTCGAGCACCTCAGGAGCCAT ATAGCCAAGAGTACCAGTTTCACCAGTCA |
| 18 | A:A | T:T | B.2 | TCTGTTTCTTGTTAAGGATGTCTTTTGTGAAGGAGA AGTAAGCCATGTCAGGTCTGCCCCATGGTCCATAT ACAGTAAAAAAACGTAAGCCTGTTATGGA[T/A]AG TCCGTAAATGTGGTTGTACGTGTGAGCAATTTCTTC TCCTGCTTTTTTAGTTGCAGCGTACAAGGAGGCGG GCTGATCAGTACGGTCCATTTCAGAGA |
| 19 | A:A | G:G | B.2 | TACCCAAGTGCTGGTTATTCAATATCATAACCTTG ACAGGCAATTTCTCAATCCTAATCATAGCCAATTC TTGAATATTCATAAGAAAACTACCATCACC[G/A]TC AATATCAATCACAGTTACACCTGGGTTTCCTACAG CTGCTCCAGCAGCAGCAGGCAATCCAAATCCCATA GCTCCTAATCCAGCTGAAGTCAGCCATT |
| 20 | C:C | T:T | K.1 | ACCGCCCAATATCAAGTGATCTCCCAACTGCTCCA GACTTATAAACCTTCACAAAATTTCTAGCACCGGG ATCAACTTCTCCCAAATTTTGCATAGTACT[T/C]GA AGACTCATCAATAGATCCATAAATTGAGTTCTGAA TATATGGAGAAGCATATGGAACATTGGATGCGCCA TTATCAATGGAATTTGAGTTCATCAAAT |
| 21 | C:C | T:T | K.1 | CATCCACATGCAGAACAAAAGGCTCAAAMYGTAC ACCGGCAACTACGACCAGTACGTCCARACCCGCGC CGAGCT[T/C]GAGGAAAACCAAATGAAGCAGTACC GMTGGGAGCAGGAGCRGATCGCCAACATGAARGA RTACATYGCCCGCTTCGGCCAYGGGTCYGCCAAAC TGGCCC |
| 22 | C:C | G:G | K.1 | GCGACAGGTTCAATGGGAATGAAGATAAAGCACC ATGGGAGCTTTATGATAAAGCTCAATCATTGGTAC AAACGGCTCAGCATTCTGCCAGTGATTATCC[G/C]T TCTCACTTAGGCGCGAGTCTTTATATTTGGATCATG ACCCTCATTCGGATCCACAAGCCCAGCGTCTTGGG CTTTCGTCGCTTTATCGATCAGAAACAC |
| 23 | T:T | C:C | K.1 | CTGTCTACGATTTATAACTCTGCCACCATATGCACC CTCTCTAAGCAGCCAACGCAACAGATAGTACCCCA AAAACCAGTCCAAAAATAGTCATTTCCTT[C/T]CTC GCTGACCCACTCGTATCGTCAGAGGCGCCAGGGCC AGGAGACACAGCSTCAGATCCAGTCGGAGCCATCG TCGGAGACGATACAGAACTGACCGTCG |

TABLE 5-continued

Markers used for selection of interspecific hybrid plants. Indicated are the SEQ ID No., the alleles corresponding with leek or garlic respectively, the linkage group they are mapped to and the sequence including the polymorphism for leek and garlic. Naturally occurring polymorphisms not linked to either the leek or garlic genotype are indicated using IUPAC nucleotide code, where R = A or G; Y = C or T; S = G or C; W = A or T; K = G or T; and M = A or C.

| SEQ ID No. | Leek | Garlic | Linkage group | Sequence |
|---|---|---|---|---|
| 24 | A:A | G:G | L.1 | TGTCACCTGAGGATGCAGATGTACATATTGTACTT GGTGTATTATACAACTTATCCAGGGAATATGATAA AGCAATACAGTCATTTGAAAATGCACTGAA[G/A]C TCAGGCCACGCGATTACTCTTTATGGAACAAGCTT GGTGCAACCAAAGCRAACAGTGTTCAAAGTTCAG AAGCAATATTAGCTTATCAGCAGGCACTAG |
| 25 | G:G | A:A | L.1 | CCTTCTCACCTTTGCTTGTACATACTGGTGCAGTTA ACTGAAGTTTCGCTAGATCGTTTTTCACTGCAATG ACTTTAGCTCCAGTTGACATGGAACCTAT[A/G]TTA AGCATCAGAATTTCCGCTTTTGTTAGCTTCGATACT TTTCCTTGCTTTTCTGCACCTTTTGTTCTTACTCCCA ATAGCCTTCTCAGTAAAAAGAAGT |
| 26 | A:A | G:G | L.1 | CTCTGTGCCTGCTGCTGTGGTGATCGCCATGTCTAT CTCTATCATCTCTATACCTCTCTCTTTCTCCTCTATC TCTATCCCTACTCCTTTCCCTCTCTCT[G/A]TCATAG TCTCTACTTCGTTCCCTTCCTCTATCCTCTCCTCTAT GCCTTCTTTCAACCATATCTTGCCCTCCTTCGAAAT CTTTCTCTCTTTCATGCCTTC |
| 27 | A:A | G:G | L.1 | ACTTAATGTAGAACCTAGAACCGCTGACAGAGAG CTTAGTCTCTAGAAGATCCGCAAGCGCTGAGCTTA ATTTTCCATTCACACCAGGACCGAGGCCACC[G/A]A TTGATATAACCTCTCCATATGCAGCTGGCTCTTCGC TTCCACCAAATACTATAGGCACTCCACCATTGACG ATCACCATAACATACGATTCGGGCTTGC |
| 28 | A:A | G:G | M.1 | TGGCAGGACCAACCCTCATTTGCCGTGTAGAACAG TACTGACCATCCATTTCAGTCATTGCACGAGTTTGT TCATTTAAATCGGCAAACTTAACAAACCC[G/A]TAG CCCTTGGAACGCCCTGTGATTCTATCAGTAACTAT CTTAGCTCCTCTAACCGAAGGATAATGGCTTTTAA AAGTCTCTTGTAATACATAATCAGTGA |
| 29 | A:A | G:G | M.1 | CAAAAGGTAAGGGTATTTCGTCGTCGGCGCTACCC TACAAGAGAACCCCACCTAGCTGGGTCAAAACCA AGCCCGAAGAGGTCCAGGAGCAAATATGTAA[G/A] TTTGCAAAGAAGGGTCTAACACCATCTCAAATTGG TGTTATTCTCCGTGATTCATCTGGTATTCCTCAGGT TAAGAGTGTCACTGGAAGCAAGATTCTWC |
| 30 | A:A | T:T | M.1 | CTACCGTTCTTCCATCGATCGTATGCTTATCATTAA GAACAGTTTCAAGAACCGAAGGATCCGCAAAAAC AACAAATCCGAAACCTCTCGGTTTACCAGT[T/A]AG CTTGTCTCGCATAATTACAGTTTGAAGAACTTCGC CATAATTACTAAAATACTGTTTCATTTTATCTTCGT CGGTTTCCCATGAGATCCCGCCTATGA |
| 31 | C:C | G:G | M.1 | GCACGTTGAGGATCCACTGGGGGAAAAAACATGG CATGCGGTACTTGAGGTGGTACAAAAGGCATGCCC CTAATAGCCTCTGGATATTGTTGCTGTGCGA[G/C]G TAATAAATTGGAGAAGGAAACTCAGCATATCCCAT AGCACTACCAGCAAGAGGATGGGGCAATGGAGGT GGTGGAGGCATAAAATGCTGTGGTCTATGA |
| 32 | C:C | T:T | M.1 | ATCCAAACTGACAAAGGGGAAATTCTAATGCTTA ACATTGGTTCAATGTCAACTGGAGCTAAAGTGATA GCAGTGAAGAACGACTTAGCTAAGCTACAA[T/C]T GACAGCACCTGTATGCACAAGCAAAGGGGAGAAA GTTGCTCTCAGCAGAAGAGTCGAAAAACATTGGCG GCTTATTGGTTGGGGTCAGATCCAGGCCGG |

TABLE 5-continued

Markers used for selection of interspecific hybrid plants. Indicated are the SEQ ID No., the alleles corresponding with leek or garlic respectively, the linkage group they are mapped to and the sequence including the polymorphism for leek and garlic. Naturally occurring polymorphisms not linked to either the leek or garlic genotype are indicated using IUPAC nucleotide code, where R = A or G; Y = C or T; S = G or C; W = A or T; K = G or T; and M = A or C.

| SEQ ID No. | Leek | Garlic | Linkage group | Sequence |
|---|---|---|---|---|
| 33 | T:T | C:C | N.1 | CAAAGCCTCTGGATCTCCCGGTATCTCTATCGATG ACAACTCTAGCATCCGTTACTTTTCCTTGTTCACTA AATAGAGTTTCAAGGGCAAGATTGTCAAC[C/T]CCC CATGATAAGTTACCAACATATAGTCTGCTGCCAGC TTCAAAGTTAGCAGCATTGCCGCTGCCACCGCTTC TGAAACTTCTGGGTGCACGCTCCTCTC |
| 34 | A:A | G:G | N.1 | TCGGGCTTTCTTCAGCCAAGCAATTCTGTCTGCTTG GTATTATTCTTGTTATCACCGAGTTGTTTGGGACGC CTACGAAATTCATCTTCACTGCTTCCAC[G/A]AAGG GCCTGATGTCGAACTCTGCATTTCCCATTTCGTCAT CAGCACTGAACAAGTCTTTGTCGTAAACTTCCACA CTAACTGGTAGTGAAGGATCTTCAA |
| 35 | A:A | G:G | O.1 | CAATTTTTGCTATGGTTCTTAGTGGATTTTATGTAT TGAGCCCGATCGACATTATTCCTGAAGGTTTACTG GGATTTGTTGGCTTGCTTGATGATTTTCT[G/A]ATTG TACTAGTTGTTTTTCTCCACCTAGCTACTCTATATC GGTCTTTGCTTCTTAACCGCCATGGAGGAGGATAT TGATTACTAGCTATTTCTCAACCGT |
| 36 | A:A | G:G | O.1 | ACAAAAACACCCATGATTCTGGCATGGTATCACCA AAATGCCCATTTGGATATGATTCTCATACTTTCAA ATTAGGCCCTTTAAGCTGCATGATTTGCAA[G/A]GC ATTGCTTTACCAAAGTAGCAAATGTATGCCTTGCT CTCATAAATTTTGCAAAGCATGTATATCCCGATTT AGAGATTGTCCACTTTGTGGTGCCGACA |
| 37 | A:A | T:T | O.1 | TTTCAGCTATCTTCAATCTAATTCCTATTACGATGG CAGATGAGGTTGCGGTCGAGACAGTCGCTCCGGCT CTCGGAGAACCCATGGATATTATGACTGC[T/A]CTA CAAGTTGTGTTAAAGAAATCACTGGCTCATGATGG CCTTGTACGTGGGCTCCATGAAGCTGCTAAGGCAA TTGAGAAGCATGCTGCACAGCTATGTA |
| 38 | T:T | C:C | P.1 | CAATGAACGATTCATATCACAGAAGAGTTTGGAAC ATAATGAGCTTCTTCAAGTCAAAAAGTCCCTGAGC TTAAAGCAAAGACTAAATTTTGGTCACAAA[C/T]TA AACAGTGTTAAAACAATTAAAGTTGAGGCTCTGAA TCCAGTTAATGTGGATCCACGTAGGGGCAAACATT CGGTGGCAGTTAACAATCATTTGAATGG |
| 39 | C:C | T:T | P.1 | TCATGACCATTTCTTCCAGCATGAAGTGTGCTTTCT CAAGATGGAACATTATATCAAGTTCACACACATTG CCAAAATGACGGTCCATAGTCTCCACCAA[T/C]AG ATGTATAAATTCCAGAATTGCTAATTCATTTTCATC ATTGTCCACCCCAACCAAGAAAAATAGTGAAGCAT AGCGCCTGTACACAACTTTGTAATTCC |
| 40 | C:C | T:T | P.1 | ACACAAGGAAGCTTGCAGAGGAAACAGAGAACCT GACCCATGAGAGAGTTCCAAGTGAACTGAAGAAG AACATCATACAAGCTCGAACAGATAAAAAGCT[T/C] ACACAGTCCCAACTTGCTCAGCTTATCAATGAGA AGCCGCAGATCATACAGGAATACGAGTCAGGAAA AGCTATTCCAAATCAGCAGATAATATCCAAAC |
| 41 | T:T | A:A | P.1 | TCAACGAATACAAGCTGCCAGCCTGATCTCAAGGG GTCGTCCAACTGACCTTCAAGGCCAAAAAGACGCC CCAACTCACTCCTAAGTTCCGGGTAACTCG[A/T]AA ATTTTGTTATATCCAACGACCTCCCAAAGGACCCA GATTTGTATACCTTTACAAACGTTCCACTTTGTTGG TTAACTTGATCCCCACCATCAGTAGAA |

TABLE 5-continued

Markers used for selection of interspecific hybrid plants. Indicated are the SEQ ID No., the alleles corresponding with leek or garlic respectively, the linkage group they are mapped to and the sequence including the polymorphism for leek and garlic. Naturally occurring polymorphisms not linked to either the leek or garlic genotype are indicated using IUPAC nucleotide code, where R = A or G; Y = C or T; S = G or C; W = A or T; K = G or T; and M = A or C.

| SEQ ID No. | Leek | Garlic | Linkage group | Sequence |
|---|---|---|---|---|
| 42 | A:A | G:G | Q.1 | AAATGGGACAGGCAGAGTCAAAATCTAAAGATGT TGAAGAAGAATTGATGCATGGCCTTAATAGAGTTT CTGAGCTTTCTCAAGAATTAGAAGCATTCAA[G/A]G CAAGATCAGAGAGTTTAGAATATGTTGTGCAGGCA GCGAGTGAAAAGGAGAAAGAGTTAACAAATACGT TGAATGAAGTTGTGGAAGAAAAGAAGAAAT |
| 43 | G:G | A:A | Q.1 | CATCATCTAACTCATAGTACACCTTTCCAGAACAC AAGACCAACCTACTAATGCCCTCTTCAACATCTTT ATGGTCATTCTGATCTTTGATTAAACGCTT[A/G]AA ACGAGTTCCTTGCTTATCGAACCCTGGATGGCCAA CAACATCATCAAATTCTGACAAATTTGACTTACAG TCTTTGT |
| 44 | G:G | T:T | Q.1 | GAAGTCGATCCCCGAGGACTGGAACTGCTTGCCAT ATTATTCATGGGAGCGAAAGCTCTATCCCTCATTC TTCTTTCCCTGTCATATTCAAATTTATCTC[T/G]AAT TTGCCCAACCTTGTCCCAGTTATCATTTTGCCTATT CCCACCACCTCCAAATAATTGATCCTTATTTGGTTC AGGATGAGTCCGGCTCCTCCTGTAT |
| 45 | G:G | A:A | R.1 | CTGATGGAGTTACACCAGAAAAATTGAGAACTCTT TTTGAGTGTCATGGAGAAGTCACCAAAATTGTTTT ACCACCATCAAAAACTGGATTAAAGAAGCG[A/G]G ATTTTGGGTTTATCCATTTTGCTGAGAGATCCAGTG CTTTAAAGGCAGTAAAAGTAGCTAAATATGAAATA GAGGGACAACCTATAGAAGTTGTATTAG |
| 46 | A:A | T:T | R.1 | CTACTTTCACATTGCCAATAAAAACTCCAGATAAT AGGCAAGTATGAGATCTTGCATTGCTTGGGACAGT ATCAGTTCCCTCACAGGGTTGCATGCCAAG[T/A]AT ATTAATGACAGCACTGACAGCCATGGCCAAGTTAT CTCTGGTACCAAGTCCGTATTCATCAACACGCTCA GTATCAGGGTCCATACTGTCCCATGCAT |
| 47 | G:G | A:A | S.1 | CTAATGTCAGTTGGGAGGATATTGGTGGTCTTGAA AATGTTAAGAGGGAACTACAAGAGACTGTTCAAT ATCCTGTGGAACATCCTGAGAAATTTGAGAA[A/G] TTCGGCATGGCACCTTCTAAAGGAGTCTTGTTCTAT GGACCTCCTGGTTGTGGGAAAACTTTGCTGGCTAA GGCAATAGCTAATGAATGCCAAGCAAACT |
| 48 | G:G | A:A | S.1 | TCACAATGTGAATATATGTAAAAACTACTCAATAT TTTAAGTAAGCTAGTACCTCAAGAAGAGAAGCAG CAAACTCCATCTGAAGTTCCTCGTCGATAGT[A/G]A AGAAAAGAGGCACGTGCACAAAGAGAGATTTAAT TTTATGCTCCTCAGCAAATCGAAGAGAGTGGTAGT AAATGTAATTACATACAAATCTTCCAGCAT |
| 49 | C:C | T:T | S.1 | ACGTTTCAAGAGATTCCAGGTGCCTGATTACAGCA AGTGCCGATCAAACTGTAAAGCTATGGAATGTTCA GACGGGAACACCGACATATTCATTTAAGTT[T/C]GA TTCACCTGCTAGGTCCGTACAGTTTTCTCTTGGTGA TAAGCTTGCTGTTATTACCGCAGATCCTTTTATGGG CCATCCTTCTACTATTCAAGTTAAGC |
| 50 | A:A | G:G | S.1 | TCTACGACTGAATAGGCTTGATCTTGAAGTGGAGC GAGATCAGTGAGAAAACAAAGCACTTCAAATCCT GAACAAGATAATAGAAAATACGCAGCCCTTC[G/A] GGATCTTTACTACTTTGCACATCCACAAGCGACCC AATCTTTGAAGTCGTGAATGAAATATGCTCATTGC CCATCACAATCTCCAGCTCTTGCCTCCCTA |

TABLE 5-continued

Markers used for selection of interspecific hybrid plants. Indicated are the SEQ ID No., the alleles corresponding with leek or garlic respectively, the linkage group they are mapped to and the sequence including the polymorphism for leek and garlic. Naturally occurring polymorphisms not linked to either the leek or garlic genotype are indicated using IUPAC nucleotide code, where R = A or G; Y = C or T; S = G or C; W = A or T; K = G or T; and M = A or C.

| SEQ ID No. | Leek | Garlic | Linkage group | Sequence |
|---|---|---|---|---|
| 51 | A:A | T:T | T.1 | ATATCCTTGTTTAATTTCAGGAACATCAGTAATATC GCCAATGGCAAAAACATTCTTCCACCCCTTAACTC TGAAACTCTCATCAACCATTAGTTGCCCT[T/A]TTTT GTTTATACAGTCCTTCAACATAGTCTCCTGAAGCC ATGATGAACCTAATGTTTTCCCAACACAGAGAAAT TTAGCATCCGCTGTAATTTTTTCACC |
| 52 | T:T | C:C | T.1 | TTCCAGGATATGCATGGACAATTACAAATTGTGCA ACATGTGAGTCCAACATGGGTTGGCTATTTACAGC TACGAAAAGAATTTGCTACCAAGATCGTT[C/T]TG GGGAATCCGTAGCTCTCAAGTTACAGATGATACCT CAATTTTGGACAAGGAACTAAAGTGAAAACACGT AATAGTTTACCTATAACAATATCTTGATC |
| 53 | T:T | A:A | T.1 | TCCAAGAACCCATTTGGGTGCAGGAAGGATGGATT TACTCCTGAAACAAATGGAGCTCCCCCAGCAATCA ATTAGCAGCAGTGCCATTGAAGGATGTAAT[A/T]TT TTATACATGCACCATGAAGAAGAGAACTAGATTAT GTCGACATGACTTGATTCATGTTATTGCATTTGATC ATCTTTCATCTTCATTCATGTTACCTA |
| 54 | C:C | G:G | T.1 | GAAATGGAGCTAACCTCGCTAACATTCGTAATTTA TCTGGAGCCGACATCGAAATTGTCGATTCACGTTC ATCAAGATATGAGCACATTGCTCAGATAAC[G/C]G GGACTCATGAGCAGAAGCGTTCAGCAGAAAATAT GATTCAGGCTTTTATCTTGTCAACT |
| 55 | G:G | T:T | U.1 | GGACGCACGTTGGAATCGGTCAGGTTAACTTTGCC CTTTCCAGTAGTGAAATTGCTGAGTCCGAGGTGGT ATCGGAGTTCTTCTTCAGATGCAGCATATG[T/G]GA TATCGATTTTGTTCCCAAGAATGAGGAATGGGACG GTCGCCAGTGATTCATCAGAAAGAAGTGCATCGAG CT |
| 56 | C:C | A:A | U.1 | ATGGGAAGAGCTTATTAAACAATGCTTTCGCCAGC CTGAAATGGTAGGGATGTTGCTTGAGCACACTGTA GGTAATCTGGATCCATTATATATAGTCAGT[A/C]GA GTGCCAAATGGTCTAGAAATACCTCGGTTAAGAGA CCGCCTTGTCAAAATCATCACCGATTATCGAACTG AAACTTCTTTAAGACATGGATGCAATGA |
| 57 | A:A | T:T | U.1 | GGGTAGACCACGAACGCGAACAACTGGCAATGAT GGAGGTTGATTATCATAGGCATATGGAATCGTGTG AGGAAGATTTGAACTGGAAGG[T/A]GCTCCATAAT AAGCACCGGTATCCATAAGATGCTGTCTCTTTAAT CTCGTATCAAGAGCACCACCGCTATCTGCATATTT CCGTTTGAAATCGCCACCGG |
| 58 | A:A | G:G | U.1 | TCAAGAAAGAAGTCTGAAGTGACGCTAGCTGCAC CAGCACTTCAATTGCCTTAAGATGTGCTGCACGGC ATGCCTGTATCTGCTGACCCCCTCGTGCAAG[G/A]C CAGTCAAATCATTCGACGATTTTGAATCGGGCAAC GAAGAATCTAAGTAATGTTCAAATTTCGGAAGCTT GACTCCAGCTACATTATCTTGACGAGAAC |
| 59 | A:A | G:G | V.1 | TGGGAGAGAAGTTTACCCTGATGGAGTTTTATATG CCTCAAAGGAAAGCCATTATTCTGTATTTAAAGCA GCAAGAATGTACAGAATGGAATGCGTTAAA[G/A]T TGATACTTTGATTTCTGGTGAAATTGACTGCAGCG ATTTTGAAAAGAAACTCCTCTTGAACAAGGACAAA CCAGCCATCATAAACGTCAATATTG |

TABLE 5-continued

Markers used for selection of interspecific hybrid plants. Indicated are the SEQ ID No., the alleles corresponding with leek or garlic respectively, the linkage group they are mapped to and the sequence including the polymorphism for leek and garlic. Naturally occurring polymorphisms not linked to either the leek or garlic genotype are indicated using IUPAC nucleotide code, where R = A or G; Y = C or T; S = G or C; W = A or T; K = G or T; and M = A or C.

| SEQ ID No. | Leek | Garlic | Linkage group | Sequence |
|---|---|---|---|---|
| 60 | C:C | T:T | V.1 | ATACACGATCAGCAATTGCCTTTGTTTGAGCAGCA ACAACATCCATTGTTGATCCAGATTCACGTTGCTC AAGAGTTTCACCAACACATGCAATTACCTT[T/C]AA ACCTTGAGAAAGAGCATATTTAACTTTGTCCCCAA CAAACTCGTTGGATTCACCTAATAAGGCTCTTCTCT CTGAGTGACCAAGAATGACCCAAGGAA |
| 61 | A:A | G:G | V.1 | TAGTTGGATCAATGGGAGGAACAGATCTAACAAA TCCTCTAAACAGTCTGGGAAATGGTAACATATTGG TCTGGAAGCGCAAAGCTGAACAATATTTAGC[G/A] GACTCTGGAATACCATATACAATTATAAGAGCTGG AGGTTTACAGGATAAAGATGGAGGCATAAGGGAA TTACTTATCGGTAAGGATGATGAGCTTCTCA |
| 62 | C:C | T:T | W.1 | AACGTGTTTATGAAATTGGAAAACAATTTAGGAAT GAGGGGATAGATATGACCCACAATCCTGAATTTAC TACATGTGAATTTTATATGGCATATGCAGA[T/C]TA CAATGATTTGATGGACCTAACGGAAAAAATGATAT CCGGAATGGTAAAGGAGTTAACAGGTGGCTATAA AATTTTGTACCATGCAAATGGAGTTGACC |
| 63 | T:T | A:A | W.1 | TAGGATCATTATCCTTCAAACCTGTTTTTAGTACAA CGGTCTGCCCTTTTGCCTTCTCCATATCCTTTTTCA ACCTATCCATGCTCTCCTTTCTACGTTC[A/T]GTCTC TAATCTATCCTTCTCAGCACGCCTTTTGTCAAGGTC AGCCTTGTAGTTTTCCATATACTCAGTAGCACTGG CTTC |
| 64 | T:T | C:C | X.1 | TCCCCACTAACTGTTGCTCAGTCAGCGGTTCGAGT TGATCGGCTAATAGCTTCAAGATTTCAGAGGTTCT AAATCCTCCTAACCATAGGAAGCACCTTTC[C/T]GC AGGTGTGGTCCACATTCCAGACAGTATATGGAAAA CATCCATTTTGGCAGCCATACTTTTGAGCTTAAATA ATTTATCATAGTGCGCCATGACACCAT |
| 65 | A:A | G:G | X.1 | CCCAATAAACAAATGCAATAACAGGTCCTTCTCTG ATTAACTTCCCATCGAGAATCACAAGATCCCCATC AACCCACCTAGGGTTTCGAAAACCAGGATC[G/A]G CTATCCTTCCTTGTCCCTTATACCTAGCAATCACAC CAAATTCTTCTGGTATAATACCCTTATGAGGAAGC TGATACTGTTTGCCTATTTTTGCACGGA |

Deposit Information

A representative seed sample of a leek garlic hybrid plant species #1430389 has been deposited at the National Collections of Industrial, Food and Marine Bacteria (NCIMB), NCIMB Limited, Ferguson Building; Craibstone Estate, Bucksburn Aberdeen, Scotland, AB21 9YA United Kingdom as: NCIMB 42564 on 21 Mar. 2016.

REFERENCES

1. Yanagine et al., *Production and characterization of an interspecific hybrid between leek and garlic.* Theor Appl Genet (2003), 107:1-5.

The invention claimed is:

1. An interspecific hybrid plant derived from a cross between an *Allium ampeloprasum* plant and an *Allium sativum* plant, wherein said interspecific hybrid plant is capable of producing seed, wherein said interspecific hybrid plant is heterozygous in its genome for at least 50 markers selected from the sequences of SEQ ID NO: 1 to SEQ ID NO: 65, each of the at least 50 markers comprising a garlic-leek interspecific single nucleotide polymorphism (SNP), wherein said interspecific hybrid plant contains at least 250 mg/kg of allicin when determined in a white part of a leaf sheet of the plant, and wherein said interspecific hybrid plant is grown from a seed of an interspecific hybrid plant as deposited under accession number NCIMB 42564.

2. The interspecific hybrid plant according to claim 1, wherein the interspecific hybrid plant is heterozygous in its genome for each of the markers represented by SEQ ID NO: 1 to SEQ ID NO: 65, each of the markers comprising a garlic-leek interspecific single nucleotide polymorphism (SNP).

3. The interspecific hybrid plant according to claim 1, wherein at least one odor compound selected from the group consisting of methyl allyl disulfide, propenyl methyl disulfide and diallyl disulfide is present in the white part of the leaf sheet of the plant.

4. The interspecific hybrid plant according to claim 3, wherein
the amount of methyl allyl disulfide is at least 25 mg/kg as determined in the white part of the leaf sheet of the plant, and/or
the amount of diallyl disulfide is at least 50 mg/kg as determined in the white part of the leaf sheet of the plant.

5. The interspecific hybrid plant according to claim 1, wherein the plant is male sterile.

6. Plant parts, edible parts, protoplasts, callus, cultured cells, cultured tissues of the interspecific hybrid plant according to claim 1.

7. A seed of an interspecific hybrid plant derived from a cross between an *Allium ampeloprasum* plant and an *Allium sativum* plant, wherein the seed is heterozygous in its genome for at least 50 markers selected from the sequences of SEQ ID NO: 1 to SEQ ID NO: 65, each of the at least 50 markers comprising a garlic-leek interspecific single nucleotide polymorphism (SNP), and wherein the seed has been deposited with NCIMB under Accession No. 42564.

* * * * *